US005703094A

United States Patent [19]

Petersen et al.

[11] Patent Number: 5,703,094
[45] Date of Patent: Dec. 30, 1997

[54] QUINOLONE- AND NAPHTHYRIDONECARBOXYLIC ACID DERIVATIVES

[75] Inventors: Uwe Petersen, Leverkusen; Michael Ruther, Monheim; Thomas Schenke, Bergisch Gladbach; Klaus Dieter Bremm, Recklinghausen; Rainer Endermann, Wuppertal, all of Germany

[73] Assignee: Bayer Aktiengesellschaft, Leverkusen, Germany

[21] Appl. No.: 583,685

[22] Filed: Jan. 5, 1996

[30] Foreign Application Priority Data

Jan. 13, 1995 [DE] Germany ............... 195 00 792.1

[51] Int. Cl.⁶ ............... A61K 31/47; C07D 215/233; C07D 471/04
[52] U.S. Cl. ............... 514/312; 514/300; 546/123; 546/156
[58] Field of Search ............... 546/123, 156; 514/300, 312

[56] References Cited

U.S. PATENT DOCUMENTS

| | | | |
|---|---|---|---|
| 4,988,709 | 1/1991 | Ogata | 514/314 |
| 4,990,517 | 2/1991 | Petersen | 514/300 |
| 5,026,856 | 6/1991 | Yatsunami | 546/156 |
| 5,371,090 | 12/1994 | Petersen | 514/300 |
| 5,464,796 | 11/1995 | Petersen et al. | 514/312 |
| 5,498,615 | 3/1996 | Kim | 514/300 |

FOREIGN PATENT DOCUMENTS

| | | |
|---|---|---|
| 0516861 | 12/1992 | European Pat. Off. . |
| 0520240 | 12/1992 | European Pat. Off. . |
| 0550019 | 7/1993 | European Pat. Off. . |
| 0588166 | 3/1994 | European Pat. Off. . |
| 4230804 | 3/1994 | Germany . |

OTHER PUBLICATIONS

V.G. Blaschke, Angew. Chem., vol. 92, pp. 14–25, (1980).
P. Newman, "Optical Resolution Procedures for Chemical Compounds" vol. 1, Optical Resolutioin Information Center, Manhattan College, Riverdale, N.Y. (1978).

*Primary Examiner*—C. Warren Ivy
*Assistant Examiner*—Evelyn Huang
*Attorney, Agent, or Firm*—Sprung Kramer Schaeffer & Briscoe

[57] ABSTRACT

The invention relates to new quinolone- and naphthyridonecarboxylic acid derivatives which are substituted in the 7-position by an unsaturated bicyclic amine radical, their salts, processes for their preparation and antibacterial compositions comprising these compounds

9 Claims, No Drawings

QUINOLONE- AND NAPHTHYRIDONECARBOXYLIC ACID DERIVATIVES

The invention relates to new quinolone- and naphthyridonecarboxylic acid derivatives which are substituted in the 7-position by an unsaturated bicyclic amine radical, their salts, processes for their preparation and antibacterial compositions comprising these compounds.

Quinolonecarboxylic acids which are substituted in the 7-position by a bicyclic unsaturated amine radical are already known from the patent applications EP 520 240 (Bayer), DE 4 230 804 (Bayer) and JP 4 253 973 (Banyu). These compounds are distinguished by a high antibacterial activity. However, they have the disadvantage that they have a relatively high genotoxic potential, which renders their use as medicaments problematic. The invention is therefore based on the object of discovering compounds which show a reduction in genotoxic properties, coupled with a high antibacterial activity.

It has now been found that the compounds of the formula (I)

T—Q         (I)

in which

Q denotes a radical of the formulae

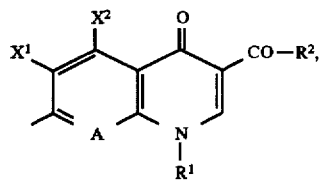

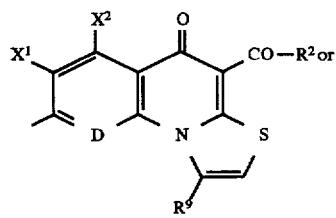

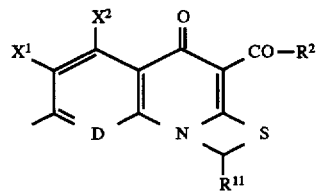

wherein $R^1$ represents alkyl which has 1 to 4 carbon atoms and is optionally mono- or disubstituted by halogen or hydroxyl, alkenyl having 2 to 4 carbon atoms, cycloalkyl which has 3 to 6 carbon atoms and is optionally substituted by 1 or 2 fluorine atoms, bicyclo[1.1.1]-pent-1-yl, 1,1-dimethylpropargyl, 3-oxetanyl, methoxy, amino, methylamino, dimethylamino or phenyl which is optionally mono- or disubstituted by halogen, amino or hydroxyl, $R^2$ represents hydroxyl, alkoxy which has 1 to 3 carbon atoms and is optionally substituted by hydroxyl, methoxy, amino or dimethylamino, benzyloxy or (5-methyl-2-oxo-1,3-dioxol-4-yl)-methyloxy, acetoxymethyloxy, pivaloyloxymethyloxy, 5-indanyloxy, phthalidinyloxy, 3-acetoxy-2-oxo-butyloxy, nitromethyl or dialkoxycarbonylmethyl having 1 to 2 carbon atoms in each alkyl part, $R^9$ represents hydrogen or alkyl which has 1 to 3 carbon atoms and is optionally substituted by methoxy, hydroxyl or halogen, $R^{11}$ represents hydrogen, $CH_3$, $CH_2F$ or $=CH_2$, $X^1$ represents hydrogen, halogen or nitro, $X^2$ represents hydrogen, halogen, amino, hydroxyl, methoxy, mercapto, methyl, halogenomethyl or vinyl, A represents N or C—$R^7$, wherein $R^7$ represents hydrogen, halogen, $CF_3$, $OCH_3$, $OCHF_2$, $CH_3$, CN, $CH=CH_2$ or $C≡CH$, or together with $R^1$ can also form a bridge having the structure —*O—$CH_2$—CH—$CH_3$, —*S—$CH_2$—$CH_2$—, —*S—$CH_2$—CH—$CH_3$, —*$CH_2$—$CH_2$—CH—$CH_3$ or —*O—$CH_2$—N—$R^8$, wherein the atom labelled with * is linked to the carbon atom of A and wherein $R^8$ denotes hydrogen, methyl or formyl, and D represents N or C—$R^{10}$, wherein $R^{10}$ represents hydrogen, halogen, $CF_3$, $OCH_3$, $OCHF_2$ or $CH_3$, or together with $R^9$ can also form a bridge having the structure —*O—$CH_2$—, —*NH—$CH_2$—, —*N($CH_3$)—$CH_2$—, —*N($C_2H_5$)—$CH_2$—, —*N($C_3H_5$)—$CH_2$— or —*S—$CH_2$—, wherein the atom labelled with * is linked to the carbon atom of D, and T denotes a radical of the formula

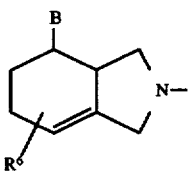

wherein

B represents $(CH_2)_m$—$NR^3R^4$ or $(CH_2)_m$—$OR^5$, wherein m represents 0 or 1, $R^3$ represents hydrogen, alkyl which has 1 to 3 carbon atoms and is optionally substituted by hydroxyl, acyl having 1 to 3 carbon atoms or alkoxycarbonyl having 1 to 4 carbon atoms in the alkyl part, $R^4$ represents hydrogen or methyl and $R^5$ represents hydrogen or methyl and $R^6$ represents hydrogen or methyl, and pharmaceutically usable hydrates and acid addition salts thereof, as well as the alkali metal, alkaline earth metal, silver and guanidinium salts of the underlying carboxylic acids, have a high antibacterial action, in particular against Gram-positive bacteria, coupled with a good tolerability.

Preferred compounds of the formula (I) are those in which

Q denotes a radical of the formulae

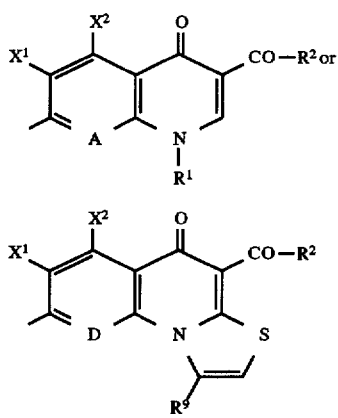

wherein

R¹ represents alkyl which has 1 to 4 carbon atoms and is optionally mono- or disubstituted by halogen, alkenyl having 2 to 3 carbon atoms, cycloalkyl which has 3 or 4 carbon atoms and is optionally substituted by 1 fluorine atom, bicyclo[1.1.1]pent-1-yl, 1,1-dimethylpropargyl, 3-oxetanyl, methylamino or phenyl which is optionally mono- or disubstituted by fluorine, amino or hydroxyl, R² represents hydroxyl, alkoxy having 1 to 2 carbon atoms, benzyloxy or (5-methyl-2-oxo-1,3-dioxol-4-yl)-methyloxy, R⁹ represents hydrogen or alkyl which has 1 to 2 carbon atoms and is optionally mono- to trisubstituted by fluorine, X¹ represents fluorine or chlorine, X² represents hydrogen, halogen, amino, methyl, trifluoromethyl or vinyl, A represents N or C—R⁷, wherein
  R⁷ represents hydrogen, halogen, CF₃, OCH₃, OCHF₂, CH₃, CN, CH=CH₂ or C≡CH, or together with R¹ can also form a bridge having the structure —*O—CH₂—CH—CH₃, —*S—CH₂—CH₂—, —*CH₂—CH₂—CH—CH₃ or —*O—CH₂—N—R⁸, wherein the atom labelled with * is linked to the carbon atom of A, and wherein
  R⁸ denotes hydrogen or methyl, and D represents N or C—R¹⁰, wherein
  R¹⁰ represents hydrogen, fluorine, chlorine, CF₃, OCH₃ or CH₃, or together with R⁹ can also form a bridge having the structure —O—CH₂—, —*N(CH₃)—CH₂—, —*N(C₂H₅)—CH₂—, —*N(C₃H₅)—CH₂— or —*S—CH₂—, wherein the atom labelled with * is linked to the carbon atom of D, and T denotes a radical of the formula

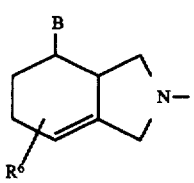

wherein

B represents —NR³R⁴ or —OH, wherein
  R³ represents hydrogen or methyl,
  R⁴ represents hydrogen or methyl and
  R⁶ represents hydrogen and pharmaceutically usable hydrates and acid addition salts thereof and the alkali metal, alkaline earth metal, silver and guanidinium salts of the underlying carboxylic acids.

Compounds of the formula (I) which are particularly preferred are those in which Q denotes a radical of the formula

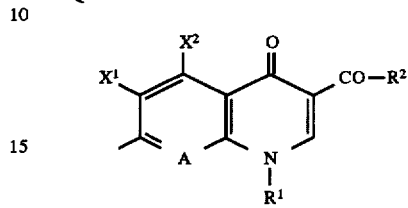

wherein

R¹ represents alkyl which has 1 to 4 carbon atoms and is optionally mono- or disubstituted by fluorine, vinyl, cyclopropyl which is optionally substituted by 1 fluorine atom or phenyl which is optionally mono- or disubstituted by fluorine, R² represents hydroxyl alkoxy having 1 to 2 carbon atoms or (5-methyl-2-oxo-1,3-dioxol-4yl)-methyloxy, X¹ represents fluorine, X² represents hydrogen, fluorine, amino, methyl or vinyl, A represents N or C—R⁷, wherein
  R⁷ represents hydrogen, fluorine, chlorine, bromine, CF₃, OCH₃, OCHF₂, CH₃, CN, CH=CH₂ or C≡CH, or together with R¹ can also form a bridge having the structure —*O—CH₂—CH—CH₃ or —*O—CH₂—N—R⁸, where the atom labelled with * is linked to the carbon atom of A, and wherein
  R⁸ denotes hydrogen or methyl, and T denotes a radical of the formula

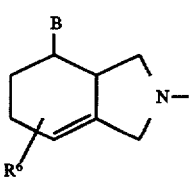

wherein

B represents NH₂
R⁶ represents hydrogen, and pharmaceutically usable hydrates and acid addition salts thereof and the alkali metal, alkaline earth metal, silver and guanidinium salts of the underlying carboxylic acids.

It has furthermore been found that the compounds of the formula (I) are obtained by a process in which compounds of the formula (II)

$$Y-Q \qquad (II)$$

in which

Q has the abovementioned meaning and

Y represents halogen, in particular fluorine or chlorine, are reacted with compounds of the formula (III)

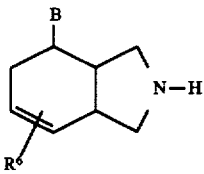

in which

B and $R^6$ have the abovementioned meanings,
if appropriate in the presence of acid-trapping agents, and any protective groups are split off.

If, for example, 6,7-difluoro-1-cyclopropyl-1,4-dihydro-8-methoxy-4-oxo-3-quinolinecarboxylic acid and (3aRS, 4RS)-2,3,3a,4,5,6-hexahydro-1H-isoindol-4-ylamine are used as starting substances, the course of the reaction can be represented by the following equation:

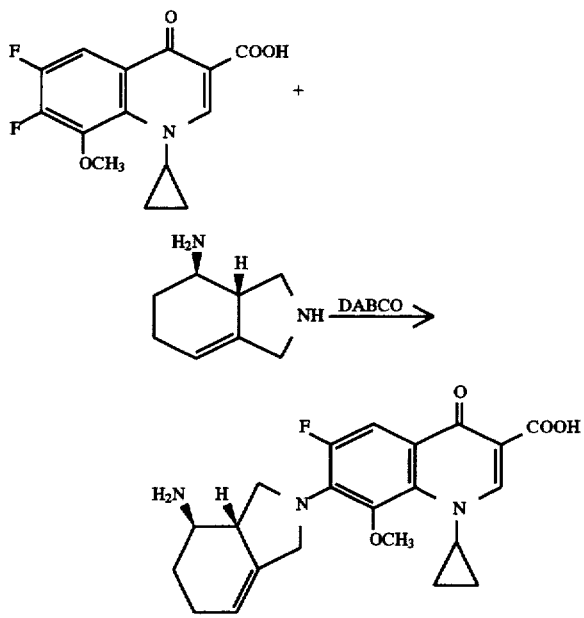

DABCO = 1,4-diazabicyclo[2.2.2]octane

The compounds of the formula (II) used as starting compounds are known or can be prepared by known methods. They can be employed, where appropriate, either as racemic or as enantiomerically pure compounds. Examples which may be mentioned are:

7-chloro-1-cyclopropyl-6-fluoro-1,4-dihydro-4-oxo-3-quinolinecarboxylic acid, 1-cyclopropyl-6,7-difluoro-1,4-dihydro-4-oxo-3-quinolinecarboxylic acid, 6-chloro-1-cyclopropyl-7,8-difluoro-1,4-dihydro-4-oxo-3-quinolinecarboxylic acid, 8-chloro-1-cyclopropyl-6,7-difluoro-1,4-dihydro-4-oxo-3-quinolinecarboxylic acid, 1-cyclopropyl-6,7,8-trifluoro-1,4-dihydro-4-oxo-3-quinolinecarboxylic acid, 5-bromo-1-cyclopropyl-6,7,8-trifluoro-1,4-dihydro-4-oxo-3-quinolinecarboxylic acid, 5-bromo-1-(2,4-difluorophenyl)-6,7,8-trifluoro-1,4-dihydro-4-oxo-3-quinolinecarboxylic acid, 1-cyclopropyl-6,7-difluoro-1,4-dihydro-8-methyl-4-oxo-3-quinolinecarboxylic acid, 6,7-difluoro-1-ethyl-1,4-dihydro-4-oxo-3-quinolinecarboxylic acid, 7-chloro-6-fluoro-1-ethyl-1,4-dihydro-4-oxo-3-quinolinecarboxylic acid, 7-chloro-6-fluoro-1,4-dihydro-1-(2-hydroxyethyl)-4-oxo-3-quinolinecarboxylic acid, 6,7-difluoro-1-(2-fluoroethyl)-1,4-dihydro-4-oxo-3-quinoline-carboxylic acid, 7-chloro-6-fluoro-1,4-dihydro-1-methoxy-4-oxo-3-quinolinecarboxylic acid, 7-chloro-6-fluoro-1,4-dihydro-1-methylamino-4-oxo-3-quinolinecarboxylic acid, 6,7-difluoro-1,4-dihydro-4-oxo-1-phenyl-3-quinolinecarboxylic acid, 7-chloro-1-cyclopropyl-6-fluoro-1,4-dihydro-4-oxo-1,8-naphthyridine-3-carboxylic acid, ethyl 7-chloro-1-cyclopropyl-6-fluoro-1,4-dihydro-4-oxo-1,8-naphthyridine-3-carboxylate, ethyl 1-cyclopropyl-6,7,8-trifluoro-1,4-dihydro-4-oxo-3-quinolinecarboxylate, 9,10-difluoro-2,3-dihydro-3-methyl-7-oxo-7H-pyrido-[1,2,3-de][1,4]benzoxacine-6-carboxylic acid, 8,9-difluoro-6,7-dihydro-5-methyl-1-oxo-1H,5H-[i,j]-quinolicine-2-carboxylic acid, 7-chloro-6-fluoro-1-phenyl-1,4-dihydro-4-oxo-1,8-naphthyridine-3-carboxylic acid, ethyl 7-chloro-6-fluoro-1-(4-fluorophenyl)-1,4-dihydro-4-oxo-1,8-naphthyridine-3-carboxylate, 6,7,8-trifluoro-1,4-dihydro-1-methyl-amino-4-oxo-3-quinolinecarboxylic acid, 1-amino-6,7,8-trifluoro-1,4-dihydro-4-oxo-3-quinolinecarboxylic acid, 6,7,8-trifluoro-1,4-dihydro-1-dimethylamino-4-oxo-3-quinolinecarboxylic acid, 6,7-difluoro-1-(4-fluorophenyl)-1,4-dihydro-8-methyl-4-oxo-3-quinolinecarboxylic acid, 7-chloro-6-fluoro-1-(4-fluorophenyl)-1,4-dihydro-4-oxo-3-quinolinecarboxylic acid, 7-chloro-6-fluoro-1-(2,4-difluorophenyl)-1,4-dihydro-4-oxo-3-quinolinecarboxylic acid, 6,7,8-trifluoro-1-(4-fluorophenyl)-1,4-dihydro-4-oxo-3-quinolinecarboxylic acid, 1-cyclopropyl-6,7-difluoro-1,4-dihydro-5-methyl-4-oxo-3-quinolinecarboxylic acid, 7-chloro-1-cyclopropyl-6-fluoro-1,4-dihydro-5-methyl-4-oxo-1,8-naphthyridine-3-carboxylic acid, 7-chloro-6-fluoro-1-(2,4-difluorophenyl)-1,4-dihydro-5-methyl-4-oxo-1,8-naphthyridine-3-carboxylic acid, 6,7-difluoro-1,4-dihydro-1-(3-oxetanyl)-4-oxo-3-quinolinecarboxylic acid, 6,7,8-trifluoro-1,4-dihydro-1-(3-oxetanyl)-4-oxo-3-quinolinecarboxylic acid, 1-(bicyclo[1.1.1]pent-1-yl)-6,7,8-trifluoro-1,4-dihydro-4-oxo-3-quinolinecarboxylic acid, 7-chloro-1-(1,1-dimethylpropargyl)-6-fluoro-1,4-dihydro-4-oxo-1,8-naphthyridine-3-carboxylic acid, 6,7,8-trifluoro-1-(2,4-difluorophenyl)-1,4-dihydro-4-oxo-3-quinolinecarboxylic acid, 6,7,8-trifluoro-1,4-dihydro-4-oxo-1-phenyl-3-quinolinecarboxylic acid, 7-chloro-1-ethyl-6-fluoro-1,4-dihydro-4-oxo-1,8-naphthyridine-3-carboxylic acid, 6,7-difluoro-1,4-dihydro-4-oxo-1-vinyl-3-quinolinecarboxylic acid, 1-cyclopropyl-5,6,7,8-tetrafluoro-1,4-dihydro-4-oxo-3-quinolinecarboxylic acid, 5-amino-1-cyclopropyl-6,7,8-trifluoro-1,4-dihydro-4-oxo-3-quinolinecarboxylic acid, 1-cyclopropyl-6,7,8-trifluoro-1,4-dihydro-5-hydroxy4-oxo-3-quinolinecarboxylic acid, 1-cyclopropyl-6,7-difluoro-1,4-dihydro-8-methoxy-4-oxo-3-quinolinecarboxylic acid, ethyl 7-chloro-1-(2,4-difluorophenyl)-6-fluoro-1,4-dihydro-4-oxo-1,8-naphthyridine-3-carboxylate, 1-cyclopropyl-6,7-difluoro-1,4-dihydro-4-oxo-8-vinyl-3-quinolinecarboxylic acid, 1-cyclopropyl-8-ethinyl-6,7-difluoro-1,4-dihydro-4-oxo-3-quinolinecarboxylic acid, 9,10-difluoro-3-methyl-7-oxo-2,3-dihydro-7H-pyrido[1,2,3-d,e][1,3,4]benzoxadiazine-6-carboxylic acid, 8-amino-9,10-difluoro-3-methyl-7-oxo-2,3-dihydro-7H-pyrido[1,2,3-d,e][1,3,4]benzoxadiazine-6-carboxylic acid, 7,8-difluoro-5-oxo-9,1-[(N-methylimino)methano]-5H-thiazolo[3,2-a]-quinoline-4-carboxylic acid, 7,8-difluoro-5-oxo-9,1-[(N-ethylimino)methano]-5H-thiazolo[3,2-a]-quinoline- 4-carboxylic acid, 7,8-difluoro-5-oxo-9,1-(epoxymethano)-5H-thiazolo[3,2-a]-quinoline-4-carboxylic acid, 7,8-difluoro-5-oxo-9,1-(epithionmethano)-5H-thiazolo[3,2-a]-quinoline-4-carboxylic acid, 7,8-difluoro-1-methyl-5-oxo-5H-thiazolo[3,2-a]-quinoline-4-carboxylic acid, 8-bromo-6,7-difluoro-1-(cis-2-fluorocyclopropyl)-1,4-dihydro-4-oxo-3-quinolinecarboxylic acid, 8-chloro-6,7-difluoro-1-(cis-2-fluorocyclopropyl)-1,4-dihydro-4-oxo-3- quinolinecarboxylic acid, 6,7-difluoro-1-(cis-2-fluorocyclopropyl)-1,4-dihydro-4-oxo-3-quinolinecarboxylic acid, 6,7,8-trifluoro-1-(cis-2-fluorocyclopropyl)-1,4-dihydro-4-oxo-3-quinolinecarboxylic acid, 5,6,7,8-tetrafluoro-1-(cis-2-fluorocyclopropyl)-1,4-dihydro-4-oxo-3-quinolinecarboxylic acid, 6,7-difluoro-1-(cis-2-fluorocyclopropyl)-1,4-dihydro-8-methyl-4-oxo-3-quinolinecarboxylic acid, 8-ethinyl-6,7-difluoro-1-(cis-2-fluorocyclopropyl)-1,4-dihydro-4-oxo-3-quinolinecarboxylic acid, 6,7-difluoro-1-(cis-2-fluorocyclopropyl)-1,4-dihydro-4-oxo-8-trifluoromethyl-3-quinolinecarboxylic acid, 6,7-difluoro-1-(cis-2-fluorocyclopropyl)-8-difluoromethoxy-1,4-dihydro-4-oxo-3-quinolinecarboxylic acid, 6,7-difluoro-1-(cis-2-fluorocyclopropyl)-1,4-dihydro-8-methoxy-4-oxo-3-quinolinecarboxylic acid, 6,7-difluoro-1-(cis-2-fluorocyclopropyl)-1,4-dihydro-5-methyl-4-oxo-3-quinolinecarboxylic acid, 5-amino-6,7,8-trifluoro-1-(cis-2-fluorocyclopropyl)-1,4-dihydro-4-oxo-3-quinolinecarboxylic acid, 8-bromo-6,7-difluoro-1-[(1R,2S)-2-fluorocyclopropyl]-1,4-dihydro-4-oxo-3-quinolinecarboxylic acid, 8-chloro-6,7-difluoro-1-[(1R,2S)-2-fluorocyclopropyl]-1,4-dihydro-4-oxo-3-quinolinecarboxylic acid, 6,7-difluoro-1-[(1R,2S)-2-fluorocyclopropyl]-1,4-dihydro-4-oxo-3-quinolinecarboxylic acid, 6,7,8-trifluoro-1-[(1R,2S)-2-fluorocyclopropyl]-1,4-dihydro-4-oxo-3-quinolinecarboxylic acid, 5,6,7,8-tetrafluoro-1-[(1R,2S)-2-fluorocyclopropyl]-1,4-dihydro-4-oxo-3-quinolinecarboxylic acid, 6,7-difluoro-1-[(1R,2S)-2-fluorocyclopropyl]-1,4-dihydro-8-methyl-4-oxo-3-quinoline-carboxylic acid, 8-ethinyl-6,7-difluoro-1-[(1R, 2S)-2-fluorocyclopropyl]-1,4-dihydro-4-oxo-3-quinolinecarboxylic acid, 6,7-difluoro-1-[(1R,2S)-2-fluorocyclopropyl]-1,4-dihydro-4-oxo-8-trifluoromethyl-3-quinolinecarboxylic acid, 6,7-difluoro-1-[(1R,2S)-2-fluorocyclopropyl]-8-difluoromethoxy-1,4-dihydro-4-oxo-3-quinolinecarboxylic acid, 6,7-difluoro-1-[(1R,2S)-2-fluorocyclopropyl]-1,4-dihydro-8-methoxy-4-oxo-3-quinolinecarboxylic acid, 6,7-difluoro-1-[(1R,2S)-2-fluorocyclopropyl]-1,4-dihydro-5-methyl-4-oxo-3-quinolinecarboxylic acid, 5-amino-6,7,8-trifluoro-1-[(1R, 2S)-2-fluorocyclopropyl]-1,4-dihydro-4-oxo-3-quinolinecarboxylic acid, 6,7-difluoro-4-oxo- 4H-[1,3]thiazeto[3,2-a]quinoline-3-carboxylic acid, 6,7-difluoro-1-methyl-4-oxo-4H-[1,3]thiazeto[3,2-a]quinoline-3-carboxylic acid, 6,7-difluoro-1-fluoromethyl-4-oxo-4H-[1,3]thiazeto[3,2-a]quinoline-3-carboxylic acid.

The compounds of the formula (III) used as starting substances are new. They can be obtained by starting from a compound of the formula (1)

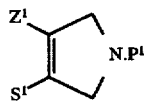

(1)

in which $Z^1$ denotes, for example, alkoxycarbonyl, $P^1$ denotes a suitable protective group on the nitrogen, for example benzyl, phenylethyl or alkoxycarbonyl having 1 to 4 carbon atoms in the alkyl part, and $S^1$ denotes hydrogen or methyl, and converting this into allyl alcohols of the formula (2)

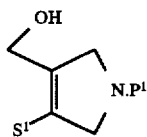

(2)

by customary reduction processes, and converting these, using suitable oxidizing agents, such as, for example, pyridine chlorochromate or dimethyl sulphoxide/oxalyl chloride/triethylamine (Swern oxidation), into the intermediate of the formula (3)

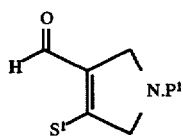

(3)

which is converted in a Wittig reaction or comparable reactions into a compound of the formula (4)

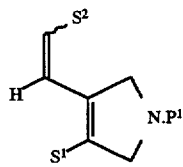

(4)

in which $S^2$ denotes hydrogen or methyl, and this is reacted with a compound of the formula (5)

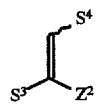

(5)

in which $Z^2$ is, for example, cyano, alkoxycarbonyl, aryloxycarbonyl or nitro and $S^3$ and $S^4$ are identical or different and represent hydrogen or methyl, in a cyclo addition reaction, to give compounds of the formula (6) formulated below in a simplified manner

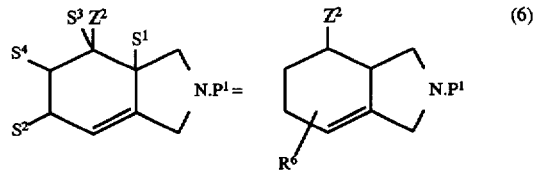

(6)

The compound Of the formula (7)

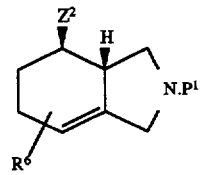

for example is separated off from the reaction mixture obtained by suitable separation methods and, in the case where $P^1$=benzyl or α-phenylethyl, is converted, by reaction with chloroformic acid esters or phosgene/alcohol, into a compound of the formula (8)

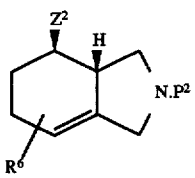
(8)

in which $P^2$ represents alkoxycarbonyl having 1 to 4 carbon atoms in the alkyl part, which is converted, by suitable acid or basic hydrolysis conditions, into an acid of the formula (9)

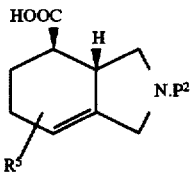
(9)

which is converted, for example, by a Curtius degradation via an intermediately formed azide of the formula (10)

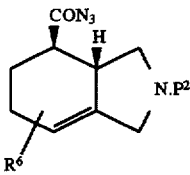
(10)

into an isocyanate of the formula (11)

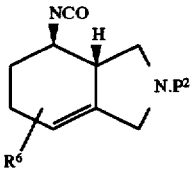
(11)

which is converted by alcoholysis into a compound of the formula (12)

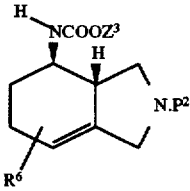
(12)

in which $Z^3$ represents $C_1$–$C_4$-alkyl, which is converted, if appropriate, with an alkylating agent, for example with methyl iodide, into a compound of the formula (13)

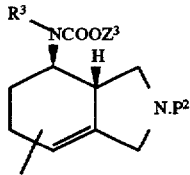
(13)

in which $R^3$ denotes hydrogen or alkyl, and this is converted by hydrolysis with suitable acids or bases into a compound of the formula (14)

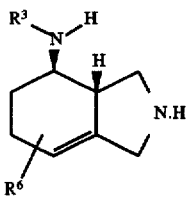
(14)

Compounds of the formula (14) correspond to the general formula (III). Compounds of the formula (III) in which B represents dialkylamino are obtained starting a compound (13) if the group $COOZ^3$, which can denote, for example, a tert-butoxycarbonyl protective group, is split off selectively and the nitrogen function liberated is then alkylated.

After the Diels-Alder reaction, which leads to the compounds of the formula (6), the isomeric compounds with the reverse configuration on the bridge-head carbon atom can also be isolated, and can be reacted in a manner corresponding to that already described for the series of compounds (6) to (14) to give compounds of the formula (15)

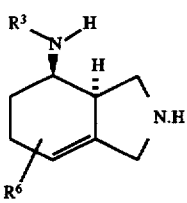
(15)

Compounds of the formula (15) correspond to the general formula (III).

Compounds of the formula (III) in which B repesents hydroxymethyl are obtained if a compound of the formula (7) in which $Z^2$ represents alkoxycarbonyl is reduced, for example with complex hydrides, such as $LiAlH_4$.

Compounds of the formula (III) in which B represents aminomethyl are obtained if a cyano group in a compound of the formula (7) is converted into an aminomethyl group, for example via a reduction with complex hydrides, such as $LiAlH_4$, and this can optionally also be alkylated. Splitting off of the protective group $P^1$ follows.

Examples which may be mentioned of unsaturated bicyclic amines of the formula (III), which can be in the form both of diastereomerically pure or enantiomerically pure compounds and of diastereomer or enantiomer mixtures, are:

2,3,3a,4,5,6-hexahydro-1H-isoindol-4-ylamine,
4-methyl-2,3,3a,4,5,6-hexahydro-1H-isoindol-4-ylamine,
5-methyl-2,3,3a,4,5,6-hexahydro-1H-isoindol-4-ylamine,
6-methyl-2,3,3a,4,5,6-hexahydro-1H-isoindol-4-ylamine,
7-methyl-2,3,3a,4,5,6-hexahydro-1H-isoindol-4-ylamine,
4-methylamino-2,3,3a,4,5,6-hexahydro-1H-isoindole,
4-dimethylamino-2,3,3a,4,5,6-hexahydro-1H-isoindole,
4-aminomethyl-2,3,3a,4,5,6-hexahydro-1H-isoindole,
4-methylaminomethyl-2,3,3a,4,5,6-hexahydro-1H-isoindole, 4-hydroxy-2,3,3a,4,5,6-hexahydro-1H-isoindole
and 4-hydroxymethyl-2,3,3a,4,5,6-hexahydro-1H-isoindole.

The enantiomerically pure starting compounds of the formula (III) can be prepared by the following processes:

1. The racemic bicyclic amines (III) can be reacted with enantiomerically pure acids, for example carboxylic acids or sulphonic acids, such as N-acetyl-L-glutamic acid, N-benzoyl-L-alanine, 3-bromo-camphor-9-sulphonic acid, camphor-3-carboxylic acid, cis-camphor acid, camphor-10-sulphonic acid, O,O'-dibenzoyl-tartaric acid, D- or L-tartaric acid, mandelic acid, α-methoxy-phenylacetic acid, 1-phenyl-ethanesulphonic acid or α-phenyl-succinic acid, to give a mixture of the diastereomeric salts, which can be separated into the diastereomerically pure salts by fractional crystallization (see P. Newman, Optical Resolution Procedures for Chemical Compounds, Volume 1). The enantiomerically pure amines can be liberated by treatment of these salts with alkali metal hydroxides or alkaline earth metal hydroxides.

2. In a manner similar to that described under 1., splitting of racemates of the basic intermediate stages which occur during preparation of the racemic bicyclic amines can be carried out with the abovementioned enantiomerically pure acids.

3. Both the racemic amines (III) and some of the intermediate stages leading to (III) can be separated by chromatography over chiral carrier materials, if appropriate after acylation (see, for example, G. Blaschke, Angew. Chem. 92, 14 [1980]).

4. The racemic amines (III) can also be converted by chemical linking to chiral acyl radicals into diastereomer mixtures, which can be separated by distillation, crystallization or chromatography into the diastereomerically pure acyl derivatives, from which the enantiomerically pure amines can be isolated by hydrolysis. Examples of reagents for linking with chiral acyl radicals are: α-methoxy-α-trifluoromethyl-phenylacetyl chloride, menthyl isocyanate, D- or L-α-phenyl-ethyl isocyanate, menthyl chloroformate and camphor-10-sulphonyl chloride.

5. In the course of the synthesis of the bicyclic amines (III), chiral protective groups can also be introduced instead of achiral protective groups. Diastereomer mixtures which can be separated are obtained in this manner. For example, in the synthesis of the intermediate stage (7), any α-phenylethyl radical present can be in the R or S configuration.

The reaction of (II) with (III), in which the compounds (III) can also be employed in the form of their salts, such as, for example, the hydrochlorides, is preferably carried out in a diluent, such as dimethyl sulphoxide, N,N-dimethylformamide, N-methylpyrrolidone, hexamethylphosphoric acid trisamide, sulpholane, acetonitrile, water, an alcohol, such as methanol, ethanol, n-propanol, isopropanol or glycol monomethyl ether, or pyridine. Mixtures of these diluents can also be used.

Acid-binding agents which can be used are all the customary inorganic and organic acid-binding agents. These include, preferably, the alkali metal hydroxides, alkali metal carbonates, organic amines and amidines. Specific agents which may be mentioned as particularly suitable are: triethylamine, 1,4-diazabicyclo[2.2.2]octane (DABCO), 1,8-diazabicyclo[5.4.0]undec-7-ene (DBU) or excess amine (III).

The reaction temperatures can be varied within a relatively wide range. In general, the reaction is carried out at between about 20° and 200° C., preferably between 80° and 160° C.

The reaction can be carried out under normal pressure, but also under increased pressure. In general, it is carried out under pressures of between about 1 and 100 bar, preferably between 1 and 10 bar.

In carrying out the process according to the invention, 1 to 15 mol, preferably 1 to 5 mol, of the compound (III) are employed per mole of compound (II).

Free amino groups can be protected by a suitable amino protective group, such as, for example, by the tert-butoxycarbonyl radical or an azomethine protective group, during the reaction and liberated again when the reaction has ended.

The preparation of compounds of the formula (I) according to the invention in which $R^2$ represents $CH_2NO_2$ or dialkoxycarbonylmethyl can also be carried out by reacting a compound of the formula (I) in which $R^2$ represents OH with an activating agent, such as carbonyldiimidazole, in a solvent, such as tetrahydrofuran, methylene chloride or chloroform, and then reacting the product with a CH-acid compound, such as nitromethane or dialkyl malonates. This reaction is preferably carried out in a solvent, such as tetrahydrofuran, in the presence of a base (sodium hydride, potassium carbonate or sodium carbonate).

The preparation of compounds of the formula (I) according to the invention in which $X^2$ denotes $NH_2$ is also carried out by reaction of compounds of the formula (I) in which $X^2$ denotes F with ammonia in polar solvents, such as dimethyl sulphoxide, at temperatures from 50° C. to 120° C. under normal pressure, or by heating in an autoclave. Compounds of the formula (I) according to the invention in which A denotes C—$OCH_3$ are also prepared by reaction of compounds of the formula (I) in which A denotes C—F with alkali metal methylates, such as, for example, sodium methylate or potassium methylate, in solvents, such as, for example, dimethylformamide, glycol dimethyl ether, dioxane, tetrahydrofuran, dimethyl sulphoxide, hexamethylphosphoric acid trisamide or alcohols, at temperatures from 20° C. to 150° C. If low-boiling solvents are used, the reaction can also be carried out in an autoclave under pressure. The reaction can be accelerated and carried out at a lower temperature by addition of crown ethers, such as, for example, 15-crown-5 or 18-crown-6.

To prepare the esters according to the invention, the underlying carboxylic acid is preferably reacted in excess alcohol in the presence of strong acids, such as sulphuric acid, anhydrous hydrogen chloride, methanesulphonic acid, p-toluenesulphonic acid or acid ion exchangers, at temperatures of about 20° to 180° C., preferably about 60° to 120° C. The water of reaction formed can also be removed by azeotropic distillation with chloroform, carbon tetrachloride or toluene.

The esters can also advantageously be prepared by heating the underlying acid with dimethylformamide dialkyl acetal in a solvent, such as dimethylformamide.

The esters used as prodrugs, such as, for example, the (5-methyl-2-oxo-1,3-dioxol-4-yl-methyl) ester, are obtained by reacting an alkali metal salt of the underlying carboxylic acid, which can optionally be protected by a protective group on the N atom, with 4-bromomethyl- or 4-chloromethyl-5-methyl-1,3-dioxol-2-one in a solvent, such as dimethylformamide, dimethylacetamide, N-methylpyrrolidone, dimethyl sulphoxide or tetramethylurea, at temperatures of about 0° to 100° C., preferably 0° to 50° C.

The acid addition salts of the compounds according to the invention are prepared in the customary manner, for example by dissolving in excess aqueous acid and precipitating the salt with a water-miscible solvent, such as methanol, ethanol, acetone or acetonitrile. It is also possible to heat an equivalent amount of betaine and acid in water or an alcohol, such as glycol monomethyl ether, and then to evaporate the mixture to dryness or to filter off the precipitated salt with suction. Pharmaceutically usable salts are to be understood as meaning, for example, the salts of hydrochloric acid, sulphuric acid, acetic acid, glycolic acid, lactic acid, succinic acid, citric acid, tartaric acid, 2-hydroxyglutaric acid, methanesulphonic acid, 4-toluenesulphonic acid, galacturonic acid, glucuronic acid, 5-oxotetrahydrofuran-2-carboxylic acid, embonic acid, glutamic acid or aspartic acid.

The alkali metal and alkaline earth metal salts of the carboxylic acids according to the invention are obtained, for example, by dissolving the betaine in excess alkali metal hydroxide solution or alkaline earth metal hydroxide solution, filtration to remove the undissolved betaine and evaporation of the filtrate to dryness. The sodium, potassium and calcium salts are pharmaceutically suitable. The corresponding silver salts are obtained by reaction of an alkali metal salt or alkaline earth metal salt with a suitable silver salt, such as silver nitrate.

In addition to the active compounds mentioned in the examples, the active compounds mentioned below and those listed in the following tables can also be prepared, and can exist either as racemates or as enantiomerically pure compounds, or else where appropriate as diastereomer mixtures or as diastereomerically pure compounds:

8-[(3aRS,4RS)-4-Amino-2,3,3a,4,5,6-hexahydro-1H-isoindol-2-yl]-7-fluoro-5-oxo-9,1-(epoxymethano)-5H-thiazolo[3,2-a]quinoline-4-carboxylic acid, 7-fluoro-8-[(3aRS,4RS)-4-methylamino-2,3,3a,4,5,6-hexahydro-1H-isoindol-2-yl]-5-oxo-9,1-(epoxymethano)-5H-thiazolo[3,2-a]quinoline-4-carboxylic acid, 8-(4-aminomethyl-2,3,3a,4,5,6-hexahydro-1H-isoindol-2-yl)-7-fluoro-5-oxo-9,1-(epoxymethano)-5H-thiazolo[3,2-a]quinoline-4-carboxylic acid, 7-fluoro-8-(4-methylaminomethyl-2,3,3a,4,5,6-hexahydro-1H-isoindol-2-yl)-5-oxo-9,1-(epoxymethano)-5H-thiazolo[3,2-a]quinoline-4-carboxylic acid, 8-[(3aRS,4RS)-4-amino-2,3,3a,4,5,6-hexahydro-1H-isoindol-2-yl]-7-fluoro-5-oxo-9,1-[(N-methylimino)methano]-5H-thiazolo[3,2-a]quinoline-4-carboxylic acid, 7-fluoro-8-[(3aRS,4RS)-4-methylamino-2,3,3a,4,5,6-hexahydro-1H-isoindol-2-yl]-5-oxo-9,1-[(N-methylimino)methano]-5H-thiazolo[3,2-a]quinoline-4-carboxylic acid, 8-(4-aminomethyl- 2,3,3a,4,5,6-hexahydro-1H-isoindol-2-yl)-7-fluoro-5-oxo-9,1-[(N-methylimino)methano]-5H-thiazolo[3,2-a]quinoline-4-carboxylic acid, 7-fluoro-8-(4-methylaminomethyl-2,3,3a,4,5,6-hexahydro-1H-isoindol-2-yl)-5-oxo-9,1-[(N-methylimino)methano]-5H-thiazolo[3,2-a]quinoline-4-carboxylic acid, 10-[(3aRS,4RS)-4-amino-2,3,3a,4,5,6-hexahydro-1H-isoindol-2-yl]-9-fluoro-3-methyl-7-oxo-2,3-dihydro-7H-pyrido[1,2,3-d,e][1,3,4]benzoxadiazine-6-carboxylic acid, 9-fluoro-3-methyl-10-[(3aRS,4RS)-4-methylamino-2,3,3a,4,5,6-hexahydro-1H-isoindol-2-yl]-7-oxo-2,3-dihydro-7H-pyrido[1,2,3-d,e][1,3,4]benzoxadiazine-6-carboxylic acid, 10-[(3aRS,4RS)-4-amino-2,3,3a,4,5,6-hexahydro-1H-isoindol-2-yl]-9-fluoro-3-methyl-7-oxo-2,3-dihydro-7H-pyrido[1,2,3-d,e][1,3,4]benzoxadiazine-6-carboxylic acid, 8-amino-10-[(3aRS,4RS)-4-amino-2,3,3a,4,5,6-hexahydro-1H-isoindol-2-yl]-fluoro-3-methyl-7-oxo-2,3-dihydro-7H-pyrido[1,2,3-d,e][1,3,4]benzoxadiazine-6-carboxylic acid, 10-(4-dimethylaminomethyl-2,3,3a,4,5,6-hexahydro-1H-isoindol-2-yl)-9-fluoro-3-methyl-7-oxo-2,3-dihydro-7H-pyrido[1,2,3-d,e][1,3,4]benzoxadiazine-6-carboxylic acid, 9-fluoro-3-methyl-10-[(3aRS,4RS)-4-methylamino-2,3,3a,4,5,6-hexahydro-1H-isoindol-2-yl]-7-oxo-2,3-dihydro-7H-pyrido[1,2,3-d,e][1,4]benzoxazine-6-carboxylic acid, 10-(4-aminomethyl-2,3,3a,4,5,6-hexahydro-1H-isoindol-2-yl)-9-fluoro-3-methyl-7-oxo-2,3-dihydro-7H-pyrido[1,2,3-d,e][1,4]benzoxazine-6-carboxylic acid, 8-amino-10-[(3aRS,4RS)-4-amino-2,3,3a,4,5,6-hexahydro-1H-isoindol-2-yl]-9-fluoro-3-methyl-7-oxo-2,3-dihydro-7H-pyrido[1,2,3-d,e][1,4]benzoxazine-6-carboxylic acid, 10-[(3aRS,4RS)-4-amino-2,3,3a,4,5,6-hexahydro-1H-isoindol-2-yl]-9-fluoro-3-methyl-7-oxo-2,3-dihydro-7H-pyrido[1,2,3-d,e][1,4]benzoxazine-6-carboxylic acid, 7-[(3aRS,4RS)-4-amino-2,3,3a,4,5,6-hexahydro-1H-isoindol-2-yl]-6-fluoro-4-oxo-4H-[1,3]thiazeto[3,2-a]quinoline-3-carboxylic acid, 7-[(3aRS,4RS)-4-amino-2,3,3a,4,5,6-hexahydro-1H-isoindol-2-yl]-6-fluoro-1-methyl-4-oxo-4H-[1,3]thiazeto[3,2-a]quinoline-3-carboxylic acid, 7-[(3aRS,4RS)-4-amino-2,3,3a,4,5,6-hexahydro-1H-isoindol-2-yl]-6-fluoro-1-fluoromethyl-4-oxo-4H-[1,3]thiazeto[3,2-a]quinoline-3-carboxylic acid, 7-[(3aRS,4RS)-4-amino-2,3,3a,4,5,6-hexahydro-1H-isoindol-2-yl]-1-cyclopropyl-6-fluoro-3-nitroacetyl-4-oxo-1,4-dihydroquinoline, 7-[(3aRS,4RS)-4-amino-2,3,3a,4,5,6-hexahydro-1H-isoindol-2-yl]-1-cyclopropyl-6-fluoro-8-methoxy-3-nitroacetyl-4-oxo-1,4-dihydroquinoline, 7-[(3aRS,4RS)-4-amino-2,3,3a,4,5,6-hexahydro-1H-isoindol-2-yl]-1-cyclopropyl-6,8-difluoro-3-nitroacetyl-4-oxo-1,4-dihydroquinoline, 7-[(3aRS,4RS)-4-amino- 2,3,3a,4,5,6-hexahydro-1H-isoindol-2-yl]-1-cyclopropyl-8-chloro-6- fluoro-3-nitroacetyl-4-oxo-1,4-dihydroquinoline, 7-[(3aRS,4RS)-4-amino-2,3,3a,4,5,6-hexahydro-1H-isoindol-2-yl]-1-cyclopropyl-3-(diethoxycarbonyl)acetyl-6-fluoro-4-oxo-1,4-dihydroquinoline, 7-[(3aRS,4RS)-4-amino-2,3,3a,4,5,6-hexahydro-1H-isoindol-2-yl]-1-cyclopropyl-3-(diethoxycarbonyl)acetyl-6-fluoro-8-methoxy-4-oxo-1,4-dihydroquinoline, 7-[(3aRS,4RS)-4-amino-2,3,3a,4,5,6-hexahydro-1H-isoindol-2-yl]-1-cyclopropyl-3-(diethoxycarbonyl)acetyl-6, 8-difluoro-4-oxo-1,4-dihydroquinoline, 7-[(3aRS,4RS)-4-amino-2,3,3a,4,5,6-hexahydro-1H-isoindol-2-yl]-8-chloro-1-cyclopropyl-3-(diethoxycarbonyl)acetyl-6-fluoro-4-oxo-1,4-dihydroquinoline, 10-[(3aRS,4RS)-4-amino-2,3,3a,4,5,6-hexahydro-1H-isoindol-2-yl]-9-fluoro-2,3-dihydro-3(S)-methyl-7-oxo-7H-pyrido[1,2,3-d,e][1,4]benzoxazine-6-carboxylic acid, 10-[(3aSR,4RS)-4-amino-2,3,3a,4,5,6-hexahydro-1H-isoindol-2-yl]-9-fluoro-2,3-dihydro-3(S)-methyl-7-oxo-7H-pyrido[1,2,3-d,e][1,4]benzoxazine-6-carboxylic acid, 7-[(3aRS,4RS)-4-amino-2,3,3a,4,5,6-hexahydro-1H-isoindol-2-yl]-1-cyclopropyl-8-fluoro-1,4-dihydro-4-oxo-3-quinolinecarboxylic acid and 7-[(3aSR,4RS)4-amino-2,3,3a,4,5,6-hexahydro-1H-isoindol-2-yl]-1-cyclopropyl-8-fluoro-1,4-dihydro-4-oxo-3-quinolinecarboxylic acid.

TABLE 1

| T* | A | $X^2$ | $R^2$ |
|---|---|---|---|
| $T^1$ | C—H | $CH_3$ | H |
| $T^1$ | C—F | F | H |
| $T^1$ | C—F | $NH_2$ | H |
| $T^1$ | C—$CH_3$ | H | H |
| $T^1$ | C—$OCH_2F$ | H | H |
| $T^1$ | N | H | $C_2H_5$ |
| $T^1$ | C—F | CH=$CH_2$ | H |
| $T^1$ | C—F | $NH_2$ | $C_2H_5$ |
| $T^1$ | C—F | H | $C_2H_5$ |
| $T^1$ | C—Cl | H | $C_2H_5$ |
| $T^1$ | C—C≡CH | H | $C_2H_5$ |
| $T^1$ | C—CH=H | H | H |
| $T^1$ | C—F | Br | $C_2H_5$ |
| $T^1$ | C—$CF_3$ | H | H |
| $T^1$ | C—$CH_3$ | F | H |
| $T^1$ | C—$CF_3$ | $NH_2$ | H |
| $T^1$ | C—$OCH_3$ | H | $C_2H_5$ |

*$T^1$ = (3aRS,4RS)-4-amino-2,3,3a,4,5,6-hexahydro-1H-isoindol-2-yl

TABLE 2

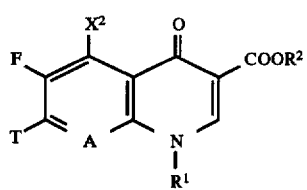

| T* | A | $X^2$ | $R^1$ | $R^2$ |
|---|---|---|---|---|
| $T^I$ | C—H | H | $C(CH_3)_3$ | H |
| $T^{II}$ | C—H | H | $C(CH_3)_3$ | H |
| $T^I$ | N | H | $C(CH_3)_3$ | H |
| $T^I$ | N | $CH_3$ | $C(CH_3)_3$ | H |
| $T^{II}$ | N | H | $C(CH_3)_3$ | H |
| $T^I$ | C—H | H | Fluoro-tert.-butyl | H |
| $T^{II}$ | C—H | H | Fluoro-tert.-butyl | H |
| $T^I$ | N | H | Fluoro-tert.-butyl | H |
| $T^{II}$ | N | H | Fluoro-tert.-butyl | H |
| $T^I$ | C—$OCH_3$ | H | Fluoro-tert.-butyl | H |
| $T^I$ | C—H | H | 2,4-Difluorophenyl | H |
| $T^{II}$ | C—H | H | 2,Difluorophenyl | H |
| $T^I$ | C—H | H | Fluorophenyl | H |
| $T^{II}$ | C—H | H | 4-Fluorophenyl | H |
| $T^I$ | N | H | 2,4-Difluorophenyl | H |
| $T^{II}$ | N | H | 2,4-Difluorophenyl | H |
| $T^I$ | N | H | 2,4-Difluorophenyl | $C_2H_5$ |

*$T^I$ = (3aRS,4RS)-4-amino-2,3,3a,4,5,6,-hexahydro-1H-isoindol-2-yl
$T^{II}$ = (3aRS,4RS)-4-methylamino-2,3,3a,4,5,6-hexahydro-1H-isoindol-2-yl

TABLE 3

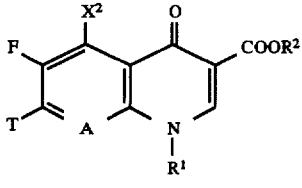

| T* | A | $X^2$ | $R^1$ | $R^2$ |
|---|---|---|---|---|
| $T^I$ | C—H | H | Bicyclo[1.1.1]pent-1-yl | H |
| $T^{II}$ | C—H | H | Bicyclo[1.1.1]pent-1-yl | H |
| $T^I$ | N | H | Bicyclo[1.1.1]pent-1-yl | H |
| $T^{II}$ | N | $CH_3$ | Bicyclo[1.1.1]pent-1-yl | H |
| $T^I$ | C—F | H | Bicyclo[1.1.1]pent-1-yl | H |
| $T^{II}$ | C—F | H | Bicyclo[1.1.1]pent-1-yl | H |
| $T^I$ | C—$OCH_3$ | H | Bicyclo[1.1.1]pent-1-yl | H |
| $T^{II}$ | C—$OCH_3$ | H | Bicyclo[1.1.1]pent-1-yl | H |
| $T^I$ | C—H | H | 3-Oxetanyl | H |
| $T^{II}$ | C—H | H | 3-Oxetanyl | H |
| $T^I$ | N | H | 3-Oxetanyl | H |
| $T^{II}$ | N | H | 3-Oxetanyl | H |
| $T^I$ | C—F | H | 3-Oxetanyl | H |
| $T^{II}$ | C—F | H | 3-Oxetanyl | H |
| $T^I$ | C—$OCH_3$ | H | 3-Oxetanyl | H |
| $T^{II}$ | C—$OCH_3$ | H | 3-Oxetanyl | H |
| $T^{II}$ | C—H | H | Fluorophenyl | $C_2H_5$ |

*$T^I$ = (3aRS,4RS)-4-amino-2,3,3a,4,5,6-hexahydro-1H-isoindol-2-yl
$T^{II}$ = (3aRS,4RS)-4-methylamino-2,3,3a,4,5,6-hexahydro-1H-isoindol-2-yl

TABLE 4

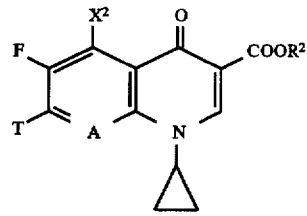

| T* | A | $X^2$ | $R^2$ |
|---|---|---|---|
| $T^{III}$ | C—H | H | H |
| $T^{IV}$ | C—H | H | H |
| $T^{III}$ | C—F | H | H |
| $T^{IV}$ | C—F | H | H |
| $T^{III}$ | C—Cl | H | H |
| $T^{IV}$ | C—Cl | H | H |
| $T^{III}$ | C—$OCH_3$ | H | H |
| $T^{IV}$ | C—$OCH_3$ | H | H |
| $T^{III}$ | C—$CHF_2$ | H | H |
| $T^{IV}$ | C—$CHF_2$ | H | H |
| $T^{III}$ | C—$CF_3$ | H | H |
| $T^{IV}$ | C—$CF_3$ | H | H |
| $T^{III}$ | C—$CH_3$ | H | H |
| $T^{IV}$ | C—$CH_3$ | H | H |
| $T^{III}$ | C—CH=$CH_2$ | H | H |
| $T^{IV}$ | C—CH=$CH_2$ | H | H |
| $T^{III}$ | C—C≡H | H | H |
| $T^{IV}$ | C—C≡H | H | H |

*$T^{III}$ = 4-amino-2,3,3a,4,5,6-hexahydro-1H-isoindol-2-yl
$T^{IV}$ = 4-amino-4-methyl-2,3,3a,4,5,6-hexahydro-1H-isoindol-2-yl

TABLE 5

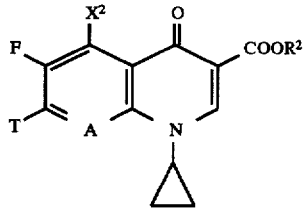

| T* | A | $X^2$ | $R^2$ |
|---|---|---|---|
| $T^{III}$ | C—F | $NH_2$ | H |
| $T^{IV}$ | C—F | $NH_2$ | H |
| $T^{III}$ | C—F | F | H |
| $T^{IV}$ | C—F | F | H |
| $T^{III}$ | N | H | H |
| $T^{IV}$ | N | H | H |
| $T^{III}$ | C—$OCH_3$ | H | H |
| $T^{IV}$ | C—$OCH_3$ | H | H |
| $T^{III}$ | C—$OCH_3$ | H | (5-Methyl-2-oxo-1,3-dioxol-4-yl)methyl |
| $T^{IV}$ | C—$OCH_3$ | H | (5-Methyl-2-oxo-1,3-dioxol-4-yl)methyl |
| $T^I$ | C—$OCH_3$ | H | (5-Methyl-2-oxo-1,3-dioxol-4-yl)methyl |
| $T^{II}$ | C—$OCH_3$ | H | (5-Methyl-2-oxo-1,3-dioxol-4-yl)methyl |
| $T^{III}$ | N | $CH_3$ | H |
| $T^{IV}$ | N | $CH_3$ | H |
| $T^I$ | C—H | $CH_3$ | H |
| $T^{II}$ | C—H | $CH_3$ | H |
| $T^{III}$ | C—H | $CH_3$ | H |
| $T^{IV}$ | C—H | $CH_3$ | H |

*$T^I$ = (3aRS,4RS)-4-amino-2,3,3a,4,5,6,-hexahydro-1H-isoindol-2-yl
$T^{II}$ = (3aRS,4RS)-4-methylamino-2,3,3a,4,5,6-hexahydro-1H-isoindol-2-yl
$T^{III}$ = 4-amino-2,3,3a,4,5,6-hexahydro-1H-isoindol-2-yl
$T^{IV}$ = 4-amino-4-methyl-2,3,3a,4,5,6-hexahydro-1H-isoindol-2-yl

TABLE 6

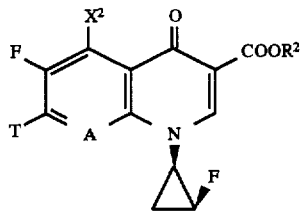

| T* | A | $X^2$ | $R^2$ |
|---|---|---|---|
| $T^I$ | C—H | H | H |
| $T^I$ | C—F | H | H |
| $T^I$ | C—Cl | H | H |
| $T^I$ | C—CH$_3$ | H | H |
| $T^I$ | C—OCH$_3$ | H | H |
| $T^I$ | N | H | H |
| $T^I$ | C—F | F | H |
| $T^I$ | C—F | NH$_2$ | H |
| $T^I$ | C—F | H | C$_2$H$_5$ |
| $T^I$ | C—Cl | H | C$_2$H$_5$ |
| $T^{II}$ | C—H | H | H |
| $T^{II}$ | C—F | H | H |
| $T^{II}$ | C—Cl | H | H |
| $T^{II}$ | C—CH$_3$ | H | H |
| $T^{II}$ | C—OCH$_3$ | H | H |
| $T^{II}$ | N | H | H |
| $T^{II}$ | C—F | F | H |

*$T^I$ = (3aRS,4RS)-4-amino-2,3,3a,4,5,6,-hexahydro-1H-isoindol-2-yl
$T^{II}$ = (3aRS,4RS)-4-methylamino-2,3,3a,4,5,6-hexahydro-1H-isoindol-2-yl

TABLE 7

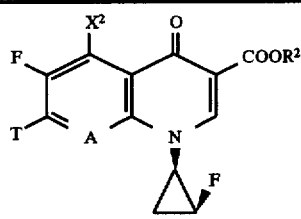

| T* | A | $X^2$ | $R^2$ |
|---|---|---|---|
| $T^{III}$ | C—H | H | H |
| $T^{III}$ | C—F | H | H |
| $T^{III}$ | C—Cl | H | H |
| $T^{III}$ | C—CH$_3$ | H | H |
| $T^{III}$ | C—OCH$_3$ | H | H |
| $T^{III}$ | N | H | H |
| $T^{III}$ | C—F | F | H |
| $T^{III}$ | C—F | NH$_2$ | H |
| $T^{III}$ | C—F | H | C$_2$H$_5$ |
| $T^{III}$ | C—Cl | H | C$_2$H$_5$ |
| $T^{IV}$ | C—H | H | H |
| $T^{IV}$ | C—F | H | H |
| $T^{IV}$ | C—Cl | H | H |
| $T^{IV}$ | C—CH$_3$ | H | H |
| $T^{IV}$ | C—OCH$_3$ | H | H |
| $T^{IV}$ | N | H | H |
| $T^{IV}$ | C—F | F | H |

*$T^{III}$ = 4-amino-2,3,3a,4,5,6-hexahydro-1H-isoindol-2-yl
$T^{IV}$ = 4-amino-4-methyl-2,3,3a,4,5,6-hexahydro-1H-isoindol-2-yl

TABLE 8

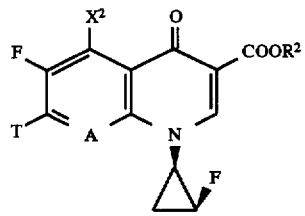

| T* | A | $X^2$ | $R^2$ |
|---|---|---|---|
| $T^V$ | C—H | H | H |
| $T^V$ | C—F | H | H |
| $T^V$ | C—Cl | H | H |
| $T^V$ | C—CH$_3$ | H | H |
| $T^V$ | C—OCH$_3$ | H | H |
| $T^V$ | N | H | H |
| $T^V$ | C—F | F | H |
| $T^V$ | C—F | NH$_2$ | H |
| $T^V$ | C—F | H | C$_2$H$_5$ |
| $T^V$ | C—Cl | H | C$_2$H$_5$ |
| $T^{VI}$ | C—H | H | H |
| $T^{VI}$ | C—F | H | H |
| $T^{VI}$ | C—Cl | H | H |
| $T^{VI}$ | C—CH$_3$ | H | H |
| $T^{VI}$ | C—OCH$_3$ | H | H |
| $T^{VI}$ | N | H | H |
| $T^{VI}$ | C—F | F | H |

*$T^V$ = 4-Methylaminomethyl-2,3,3a,4,5,6-hexahydro-1H-isoindol-2-yl
$T^{VI}$ = 4-Ethylaminomethyl-2,3,3a,4,5,6-hexahydro-1H-isoindol-2-yl

TABLE 9

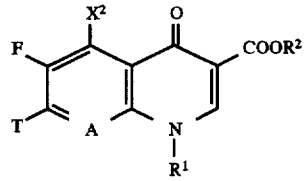

| T* | A | $X^2$ | $R^1$ | $R^2$ |
|---|---|---|---|---|
| $T^{VII}$ | C—H | H | Cyclopropyl | H |
| $T^{VII}$ | C—F | H | Cyclopropyl | H |
| $T^{VII}$ | C—Cl | H | Cyclopropyl | H |
| $T^{VII}$ | C—OCH$_3$ | H | Cyclopropyl | H |
| $T^{VII}$ | N | H | Cyclopropyl | H |
| $T^{VII}$ | N | H | C(CH$_3$)$_3$ | H |
| $T^{VII}$ | C—H | H | (1R,2S)-2-Fluorocyclopropyl | H |
| $T^{VII}$ | C—F | H | (1R,2S)-2-Fluorocyclopropyl | H |
| $T^{VII}$ | C—OCH$_3$ | H | (1R,2S)-2-Fluorocyclopropyl | H |
| $T^{VII}$ | N | H | (1R,2S)-2-Fluorocyclopropyl | H |
| $T^{VII}$ | C—H | H | 2,Difluorophenyl | H |
| $T^{VII}$ | N | H | 2,Difluorophenyl | H |
| $T^{VII}$ | C—H | H | Fluorophenyl | H |
| $T^{VII}$ | C—H | H | Fluorophenyl | H |
| $T^{VII}$ | C—H | H | Ethyl | H |
| $T^{VII}$ | C—C≡CH | H | Cyclopropyl | H |
| $T^{VII}$ | C—F | CH=CH$_2$ | Cyclopropyl | H |
| $T^{VII}$ | C—F | F | Cyclopropyl | H |
| $T^{VII}$ | C—F | NH$_2$ | Cyclopropyl | H |
| $T^{VII}$ | C—H | CH$_3$ | Cyclopropyl | H |

*$T^{VII}$ = (3asR,4RS)-4-amino-2,3,3a,4,5,6-hexahydro-1H-isoindol-2-yl

The compounds according to the invention have a potent antibiotic action and display a broad antibacterial spectrum against Gram-positive and Gram-negative germs, above all including those which are resistant to various antibiotics, such as, for example, penicillins, cephalosporins, aminoglycosides, sulphonamides, tetracyclines and against commercially available quinolones, coupled with a low toxicity. The compounds according to the invention are distinguished in particular by the fact that they have lower interactions with mammalian DNA compared with the compounds according to the prior art.

These valuable properties enable them to be used as chemotherapeutic active compounds in medicine and in veterinary medicine. Furthermore, they can be used as substances for the preservation of inorganic and organic materials, for example polymers, lubricants, paints, fibres, leather, paper and wood, and of foodstuffs and water.

The compounds according to the invention are active against a very broad spectrum of microorganisms. Gram-negative and Gram-positive bacteria and bacteria-like microorganisms can be combated and the diseases caused by these pathogens can be prevented, alleviated and/or cured with the aid of these compounds.

The compounds according to the invention are distinguished by an strong action against dormant germs. The compounds have a potent bactericidal action on dormant bacteria, that is to say bacteria which show no detectable growth. This relates not only to the amount to be employed, but also to the rate of destruction. Such results have been found on Gram-positive and Gram-negative bacteria, in particular on *Staphylococcus aureus, Pseudomonas aeruginosa, Enterococcus faecalis* and *Escherichia coli*.

The compounds according to the invention are particularly active against typical and atypical Mycobacteria and *Helicobacter pylori*, and also against bacteria-like microorganisms, such as, for example, Mycoplasma and Rickettsia. They are therefore particularly suitable in human and veterinary medicine for the prophylaxis and chemotherapy of local and systemic infections caused by these pathogens.

The compounds are furthermore particularly suitable for combating protozoonoses and helminthoses.

The compounds according to the invention can be used in various pharmaceutical formulations. Preferred pharmaceutical formulations which may be mentioned are tablets, coated tablets, capsules, pills, granules, suppositories, solutions, suspensions and emulsions, pastes, ointments, gels, creams, lotions, powders and sprays.

The compounds according to the invention can also be linked to β-lactam derivatives, such as, for example, cephalosporins or penems, by covalent bonds to give so-called dual action derivatives.

Tables 9 and 10 show the minimum inhibitory concentrations (MIC values), as a measure of the antibacterial activity, and the $ID_{50}$ values, as a measure of the interactions with mammalian DNA of a substance, both for compounds according to the invention and for reference compounds from the prior art (EP 520 240). These data demonstrate that the compounds according to the invention show less interactions with mammalian DNA, coupled with a high antibacterial activity.

The minimum inhibitory concentrations (MIC) were determined by a series dilution method on Iso-Sensitest agar (Oxoid). For each test substance, a series of agar plates each comprising concentrations of the active compound decreasing by double dilution in each case was prepared. The agar plates were inoculated with a multipoint inoculator (Denley). Overnight cultures of the pathogens which had been diluted beforehand such that each inoculation point comprised about $10^4$ colony-forming particles were used for the inoculation. The inoculated agar plates were incubated at 37° C. and the germ growth was read off after about 20 hours. The MIC value (µg/ml) indicates the lowest active compound concentration at which no growth was detectable with the naked eye.

The $ID_{50}$ is understood as meaning the concentration of a substance at which DNA synthesis in cells from ovaries of the Chinese hamster (CHO-KI) is inhibited by 50%. This value is determined after incubation of the corresponding substances in decreasing dilution stages over defined periods of time. For this, the DNA synthesis in CHO-KI cells is determined in comparison with controls by means of fluorophotometric methods.

TABLE 9

MIC values (µg/ml) and $ID_{50}$ values of active compounds according to the invention

| | | Example | | | |
|---|---|---|---|---|---|
| Species | Strain | 1 | 2 | 3 | 4 |
| E. coli | Neumann | ≦0.015 | ≦0.015 | ≦0.015 | ≦0.015 |
| Staph. aureus | 133 | ≦0.015 | ≦0.015 | ≦0.015 | ≦0.015 |
| Staph. aureus | ICB 25701 | ≦0.015 | 0.125 | ≦0.015 | 0.03 |
| Ps. aeruginosa | Walter | 0.125 | 1 | 0.5 | 0.25 |
| $ID_{50}$ (µg/ml) | | 4 | 2 | 0.1 | 2 |

TABLE 10

MIC values (µg/ml) and $ID_{50}$ values of active compounds from the prior art

| | | Examples from EP 520 240*) | | |
|---|---|---|---|---|
| Species | Strain | 17 B | 19 | 18 A |
| E. coli | Neumann | ≦0.015 | ≦0.015 | ≦0.015 |
| Staph. aureus | 133 | ≦0.015 | ≦0.015 | ≦0.015 |
| Staph. aureus | ICB 25701 | 0.03 | 1 | ≦0.015 |
| Ps. aeruginosa | Walter | 0.25 | 1 | 0.25 |
| $ID_{50}$ (µg/ml) | | 0.01 | 1 | 0.06 |

*)Reference compounds from EP 520 240:
17 B: 7-(4-amino-1,3,3a,4,7,7a-hexahydro-isoindol-2-yl)-1-cyclopropyl-6,8-difluoro-1,4-dihydro-4-oxo-3-quinolinecarboxylic acid,
19: 7-(4-amino-1,3,3a,4,7,7a-hexahydro-isoindol-2-yl)-1-cyclopropyl-6-fluoro-1,4-dihydro-4-oxo-3-quinolinecarboxylic acid,
18 A: 7-(4-amino-1,3,3a4,7,7a-hexahydro-isoindol-2-yl)-8-chloro-1-cyclopropyl-6-fluoro-1,4-dihydro-4-oxo-3-quinolinecarboxylic acid

PREPARATION OF THE INTERMEDIATE PRODUCTS

Example Z 1

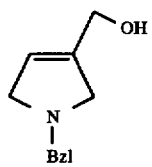

87.0 g (0.38 mol) of ethyl 1-benzyl-2,5-dihydro-1H-pyrrole-3-carboxylate are initially introduced into 430 ml of tetrahydrofuran, the mixture is cooled to −70° C., and 1200 ml of a 1 molar solution of diisobutylaluminium hydride in hexane are added dropwise. The mixture is subsequently stirred at −70° C. for 3 hours and at room temperature for a further 15 hours. It is cooled to 0° C. and hydrolyzed by addition of 390 ml of saturated ammonium chloride solution and 390 ml of 6 normal sulphuric acid. The aqueous phase is separated off, rendered basic with potassium hydroxide and extracted several times with tert-butylmethyl ether. The combined organic extracts are dried, concentrated and distilled.

Yield: 58.0 g (81% of theory) of 1-benzyl-2,5-dihydro-3-hydroxymethyl-1H-pyrrole, Boiling point: 120°–122° C./0.1 mbar, ¹H-NMR (CDCl₃): δ 7.50–7.18 (m, 5H), 5.55 (m, 1H), 4.10 (m, 2H), 3.80 (s, 2H) 3.70–3.35 ppm (m, 5H).

Example Z 2

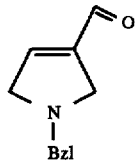

64.3 g (0.49 mol) of oxalyl chloride are dissolved in 580 ml of methylene chloride and the solution is cooled to −70° C. First a solution of 76.5 g of dimethyl sulphoxide in 174 ml of methylene chloride and then a solution of 58.0 g (0.31 mol) of 1-benzyl-2,5-dihydro-3-hydroxymethyl-1H-pyrrole in 174 ml of methylene chloride, and subsequently 198 g of triethylamine are added dropwise. The mixture is subsequently stirred for 30 minutes, heated to room temperature and poured onto 600 g of ice. The organic phase is separated off and the aqueous phase is rendered more strongly basic with potassium carbonate and extracted several times with methylene chloride. The combined organic phases are dried and concentrated and the residue is used for the next reaction without further purification.

Yield (crude): 59.5 g of 1-benzyl-2,5-dihydro-1H-pyrrole-3-carbaldehyde,

¹H-NMR (CDCl₃): δ 9.74 (s, 1H), 7.60–7.10 (m, 5H), 6.85 (m, 1H), 3.81 (s, 2H), 3.80–3.60 ppm (m, 4H).

Example Z 3

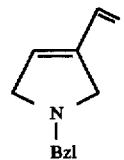

129 g (0.36 mol) of methyltriphenylphosphonium bromide are initially introduced into 828 ml of tetrahydrofuran, the mixture is cooled to −10° C., 111 g of a 23% strength n-butyllithium solution in hexane are added dropwise and the mixture is subsequently stirred at −10° C. for 20 minutes and at −70° C. for 90 minutes. A solution of 59.1 g (0.31 mol) of 1-benzyl-2,5-dihydro-1H-pyrrole-3-carbaldehyde in 197 ml of tetrahydrofuran is then added dropwise and the mixture is warmed to room temperature overnight. The mixture is poured into 2000 ml of a saturated sodium chloride solution and extracted several times with petroleum ether. The combined organic phases are dried, the triphenylphosphine oxide which precipitates is filtered off with suction, the filtrate is concentrated again and the residue is used for the next reaction without further purification.

Yield: 57.0 g (82% of theory, purity 83% according to GC) of 1-benzyl-2,5-dihydro-3-vinyl-1H-pyrrole, ¹H-NMR (CDCl₃): δ 7.40–7.20 (m, 5H), 6.48 (dd, 1H), 5.73 (s, 1H), 5.03 (dd, 2H), 3.85 (s, 2H), 3.58 ppm (s, 4H).

Example Z 4

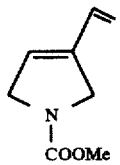

20.0 g (0.08 mol, 73% pure) of 1-benzyl-2,5-dihydro-3-vinyl-1H-pyrrole, dissolved in 180 ml of methylene chloride, are mixed with 13.8 g of sodium carbonate and the mixture is cooled to 0° C. A solution of 12.3 g of methyl chloroformate in 40 ml of methylene chloride is added dropwise and the mixture is subsequently stirred at room temperature for 15 hours. The solid is filtered off and washed out several times with methylene chloride, and the filtrates are combined. They are washed with water, dried and concentrated and the residue is chromatographed over silica gel with a mixture of ethyl acetate and petroleum ether (1:10).

Yield: 7.70 g (46% of theory) of 2,5-dihydro-1-methoxycarbonyl-3-vinyl-1H-pyrrole, ¹H-NMR (CDCl₃): δ 6.49 (dd, 1H), 5.80–5.67 (m, 1H), 5.25–5.00 (m, 2H), 4.35–4.15 (m, 4H), 3.74 ppm (d, 3H).

Example Z 5

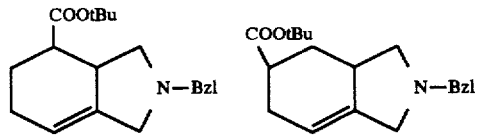

20.0 g (0.08 mol) of 1-benzyl-2,5-dihydro-3-vinyl-1H-pyrrole are dissolved in 200 ml of xylene, and a solution of 39.4 g (0.31 mol) of tert-butyl acrylate in 200 ml of xylene is added. The mixture is heated under reflux overnight, cooled and concentrated.

Yield: 17.6 g (0.06 mol) of a mixture of four isomers which can be separated by chromatography. Column chromatography over silica gel with mixtures of ethyl acetate and petroleum ether (1:30 to 1:5) allows tert-butyl (5RS,6RS)-8-benzyl-8-azabicyclo[4.3.0]non-1-ene-5-carboxylate [tert-butyl(3aRS,4RS)-2-benzyl-2,3,3a,4,5,6-hexahydro-1H-isoindole-4-carboxylate]and tert-butyl (5RS,6SR)-8-benzyl-8-azabicyclo[4.3.0]non-1-ene-5-carboxylate [tert-butyl(3aRS,4SR)-2-benzyl-2,3,3a,4,5,6-hexahydro-1H-isoindole-4-carboxylate] to be separated off from the two tert-butyl 8-benzyl-8-azabicyclo[4.3.0]non-1-ene-4-carboxylates formed.

¹H-NMR of the (5RS,6RS) isomer (CDCl₃): δ 7.40–7.20 (m, 5H), 5.40 (m, 1H), 3.66 (q, 2H), 3.56 (dm, 1H), 3.29 (dd, 1H), 2.92 (dm, 1H), 2.70–2.80 (m, 1H), 2.20–1.90 (m, 5H), 1.75–1.45 (m, 1H), 1.43 ppm (s, 9H).

¹H-NMR of the (5RS,6SR) isomer (CDCl₃): δ 7.42–7.20 (m, 5H), 5.43 (m, 1H), 3.67 (q, 2H), 3.56 (dm, 1H), 3.06–2.70 (m, 3H), 2.42–1.95 (m, 4H), 1.85–1.65 (m, 2H), 1.43 ppm (s, 9H).

Example Z 6

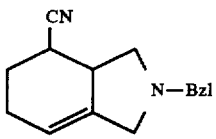 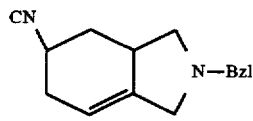

7.00 g (0.04 mol) of 1-benzyl-2,5-dihydro-3-vinyl-1H-pyrrole are dissolved in 50 ml of xylene, and a solution of 5.00 g (0.09 mol) of acrylonitrile in 50 ml of xylene is added. The mixture is heated under reflux overnight, cooled and concentrated.

Yield: 3.7 g (41% of theory) of a mixture of four isomers which can be separated by chromatography. Column chromatography over silica gel with mixtures of ethyl acetate and petroleum ether (1:30 to 1:5) allows 8-benzyl-8-azabicyclo[4.3.0]non-1-ene-5-carboxylic acid nitrile to be separated off from 8-benzyl-8-azabicyclo[4.3.0]non-1-ene-4-carboxylic acid nitrile.

$^1$H-NMR of (5RS,6RS)-8-benzyl-8-azabicyclo[4.3.0]non-1-ene-5-carboxylic acid nitrile (CDCl$_3$): δ 7.40–7.20 (m, 5H), 5.45 (m, 1H), 3.78 (d, 1H), 3.58 (d, 1H), 3.55 (dm, 1H), 3.22 (dd, 1H), 2.90 (dm, 1H), 2.80–2.65 (m, 4H), 1.90–1.65 ppm (m, 1H)

Example Z 7

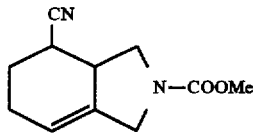

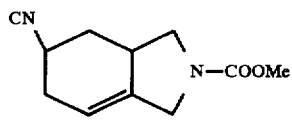

3.00 g (0.01 mol) of a mixture of 8-benzyl-8-azabicyclo[4.3.0]non-1-ene-5-carboxylic acid nitrile and 8-benzyl-8-azabicyclo[4.3.0]non-1-ene-4-carboxylic acid nitrile are dissolved in 20 ml of methylene chloride, the solution is stirred with 1.93 g of sodium carbonate, and 2.00 g of ethyl chloroformate, dissolved in 3 ml of methylene chloride, are added. The mixture is subsequently stirred at room temperature for 15 hours and the solid is filtered off and rinsed several times with methylene chloride. The combined filtrates are washed with water, dried and concentrated and the residue is chromatogaphed over silica gel with a mixture of ethyl acetate and petroleum ether (1:4).

Yield: 1.1 g (40% of theory) of a mixture of 8-methoxycarbonyl-8-azabicyclo[4.3.0]non-1-ene4-carboxylic acid nitrile and 8-methoxycarbonyl-8-azabicyclo[4.3.0]non-1-ene-5-carboxylic acid nitrile.

Example Z 8

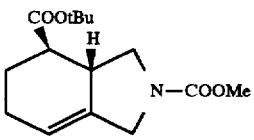

23.0 g (0.07 mol) of tert-butyl(5RS,6RS)-8-benzyl-8-azabicyclo[4.3.0]non-1-ene-5-carboxylate in 180 ml of methylene chloride are mixed with 12.5 g (0.12 mol) of sodium carbonate, the mixture is cooled to 0° C. and a solution of 11.9 g (0.12 g) of methyl chloroformate in 45 ml of methylene chloride is added dropwise. After 30 minutes at 0° C., the mixture is warmed to room temperature and subsequently stirred overnight. The solid is filtered off and washed out, the combined organic filtrates are washed with water, dried and concentrated and the benzyl chloride formed during the reaction is removed by distillation.

Yield: 17.0 g (76% of theory) of tert-butyl(5RS,6RS)-8-methoxycarbonyl-8-azabicyclo [4.3.0]non-1-ene-5-carboxylate, $^1$H-NMR (CDCl$_3$): δ 5.60 (m, 1H), 4.05–3.75 (m, 3H), 3.70 (s, 3H), 2.90–2.72 (m, 2H), 2.60–2.42 (m, 2H), 2.35–2.10 (m, 3H), 1.45 ppm (s, 9H).

Example Z 9

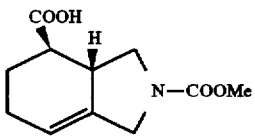

17.0 g (0.06 mol) of tert-butyl (5RS,6RS)-8-methoxycarbonyl-8-azabicyclo[4.3.0]non-1-ene-5-carboxylate are initially introduced into 420 ml of methylene chloride, 120 ml of trifluoroacetic acid are added dropwise and the mixture is subsequently stirred at room temperature for 3 hours. It is concentrated, the residue is taken up again in methylene chloride and the mixture is washed several times with water. The residue is filtered over silica gel with a mixture of cyclohexane and acetone (3:1).

Yield: 7.9 g (58% of theory) of (5RS,6RS)-8-methoxycarbonyl-8-azabicyclo[4.3.0]non-1-ene-5-carboxylic acid.

Melting point: 144°–147° C., $^1$H-NMR (CDCl$_3$): δ 10.5–9.20 (m, 1H), 5.65 (dm, 1H), 4.10–3.75 (m, 3H), 3.71 (s, 3H), 3.00–2.90 (m, 1H), 2.90–2.80 (m, 1H), 2.30–2.14 (m, 4H), 1.75–1.65 ppm (m, 1H).

Example Z 10

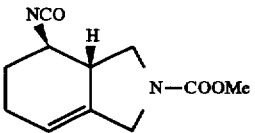

8.50 g (0.04 mol) of (5RS,6RS)-8-methoxycarbonyl-8-azabicyclo[4.3.0]non-1-ene-5-carboxylic acid are initially introduced into 200 ml of toluene, and the mixture is mixed with 4.20 g of triethylamine and 12.5 g of diphenylphosphoryl azide. The mixture is heated under reflux for 5 hours, the cooled solution is poured onto ice-water and the organic phase is separated off and extracted several more times with toluene. The combined extracts are dried and concentrated and the residue is used for the following reaction without further purification.

Crude yield: 10.6 g of a brown oil, (5RS,6RS)-8-methoxycarbonyl-8-azabicyclo[4.3.0]non-1-en-5-ylisocyanate, IR: 2250 cm$^{-1}$, $^1$H-NMR (CD$_3$OD): δ 5.62 (m, 1H), 4.08–3.76 (m, 3H), 3.67 (s, 3H), 3.42 (ddd, 1H), 2.96 (tm, 1H), 2.80–2.50 (m, 1H), 2.35–2.15 (m, 2H), 2.02–1.83 (m, 1H), 1.65–1.40 ppm (m, 1H).

Example Z 11

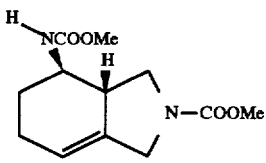

10.6 g of crude (5RS,6RS)-8-methoxycarbonyl-8-azabicyclo[4.3.0]non-1-en-5-yl isocyanate are dissolved in 200 ml of methanol and the solution is heated under reflux for 15 hours. The cooled mixture is concentrated and the residue is chromatographed over silica gel with a mixture of cyclohexane and acetone (3:1).

Yield: 6.11 g (64% of theory, based on the acid) (5RS,6RS)-5-methoxycarbonylamino-8-azabicyclo[4.3.0]non-1-ene-8-carboxylate, Melting point: 118°–121° C., $^1$H-NMR (CDCl$_3$): δ 5.59 (d, 1H), 4.65 (m, 1H), 4.07–3.85 (m, 3H), 3.72 (s, 3H), 3.68 (s, 3H), 3.50 (m, 1H), 3.08 (qm, 1H), 2.52 (m, 1H), 2.35–2.15 (m, 2H), 2.05–1.95 (m, 1H), 1.53–1.41 ppm (m, 1H).

Example Z 12

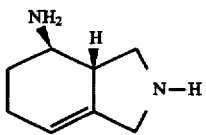

6.00 g (0.02 mol) of methyl (5RS,6RS)-5-methoxycarbonylamino-8-azabicyclo[4.3.0]non-1-ene-8-carboxylate are dissolved in 20 ml of ethanol, and 400 g of a saturated barium hydroxide solution are added. The mixture is heated under reflux for two days and cooled, the barium carbonate which has precipitated out is filtered off and the filtrate is extracted several times with chloroform. The organic phases are dried and concentrated.

Yield: 3.20 g (98% of theory) of (5RS,6RS)-5-amino-8-azabicyclo[4.3.0]non-1-ene [(3aRS,4RS)-2,3,3a,4,5,6-hexahydro-1H-isoindol-4-ylamine], $^1$H-NMR (CDCl$_3$): δ 5.46 (m, 1H), 3.72–3.55 (m, 1H), 3.55–3.33 (m, 2H), 2.65–2.36 (m, 2H), 2.33–2.05 (m, 3H), 1.91–1.76 (m, 1H), 1.64 (s, 3H), 1.53–1.30 ppm (m, 1H).

Example Z 13

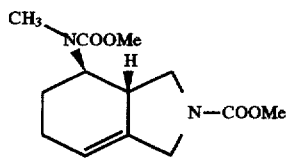

240 mg (7.87 mmol) of 80% pure sodium hydride are initially introduced into 10 ml of tetrahydrofuran. 1.00 g of methyl (5RS,6RS)-5-methoxycarbonylamino-8-azabicyclo[4.3.0]non-1-ene-8-carboxylate, dissolved in 10 ml of tetrahydrofuran, is added dropwise and the mixture is heated under reflux for 30 minutes. It is allowed to cool to room temperature, 1.12 g (7.87 mmol) of methyl iodide are added and the mixture is heated under reflux for 15 hours. It is then cooled to room temperature, excess sodium hydride is decomposed with a little water, and the mixture is poured onto ice-water and extracted several times with ethyl acetate.

Yield: 1.00 g (95% of theory).

(5RS,6RS) isomer: $^1$H-NMR (CDCl$_3$): δ 5.58 (d, 1H), 4.08–3.89 (m, 3H), 3.85–3.75 (m, 1H), 3.72 (s, 3H), 3.70 (s, 3H), 3.02 (t, 1H), 2.90–2.82 (m, 1H), 2.84 (s, 3H), 2.35–2.25 (m, 2H), 1.80–1.72 ppm (m, 2H).

Example Z 14

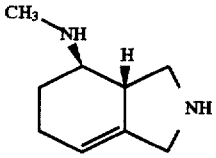

1.5 g (6 mmol) of methyl (5RS,6RS)-5-(N-methoxycarbonyl—N—methyl-amino)-8-azabicyclo[4.3.0]non-1-ene-8-carboxylate are dissolved in 10 ml of ethanol, and 130 g of a saturated barium hydroxide solution are added. The mixture is heated under reflux for two days and cooled, the barium carbonate which has precipitated out is filtered off and the filtrate is extracted several times with chloroform. The combined organic phases are dried and concentrated. 0.6 g of a brown oil which is chromatographed over silica gel with a mixture of methylene chloride/methanol/aqueous ammonia (14:5:1) is obtained.

Yield: 0.1 g (9% of theory) of (5RS,6RS)-5-methylamino-8-azabicyclo[4.3.0]non-1-ene [(3aRS,4RS)-4-methylamino-2,3,3a,4,5,6-hexahydro-1H-isoindole], $^1$H-NMR (CDCl$_3$/CD$_3$OD): δ 5.88 (m, 1H), 4.02–3.85 (m, 3H), 3.18–3.04 (m, 3H), 3.75 (s, 3H), 2.48–2.23 (m, 3H), 1.82–1.72 ppm (m, 1H).

Example Z 15

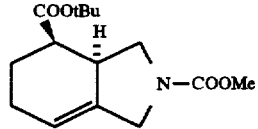

17.0 g (0.05 mol) of tert-butyl (5RS,6SR)-8-benzyl-8-azabicyclo[4.3.0]non-1-ene-5-carboxylate are dissolved in 140 ml of methylene chloride, the solution is mixed with 9.4 g (0.09 mol) of sodium carbonate, the mixture is cooled to 0° C. and a solution of 8.9 g (0.09 mol) of methyl chloroformate in 35 ml of methylene chloride is added dropwise. After 30 minutes at 0° C., the mixture is warmed to room temperature and subsequently stirred overnight. The solid is filtered off and washed out, the combined organic filtrates are washed with water, dried and concentrated and the benzyl chloride formed during the reaction is removed by distillation.

Yield: 4.9 g (32% of theory) of tert-butyl (5RS,6SR)-8-methoxycarbonyl-8-azabicyclo[4.3.0]non-1-ene-5-carboxylate, ¹H-NMR (CDCl₃): δ 5.63 (m, 1H), 4.05–3.90 (m, 2H), 3.82–3.65 (m, 1H), 3.71 (s, 3H), 3.29 (t, 1H), 2.95–2.75 (m, 2H), 2.39–1.92 (m, 3H), 1.89–1.69 (m, 1H), 1.45 ppm (s, 9H).

Example Z 16

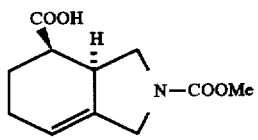

4.0 g (0.01 mol) of tert-butyl (5RS,6SR)-2-methoxycarbonyl-2-azabicyclo[4.3.0]non-4-ene-8-carboxylate are initially introduced into 100 ml of methylene chloride at 0° C., 30 ml of trifluoroacetic acid are added dropwise and the mixture is subsequently stirred at room temperature for 3 hours. It is concentrated, the residue is taken up again in methylene chloride and the mixture is washed several times with water. The residue is filtered over silica gel with a mixture of cyclohexane and acetone (3:1).

Yield: 3.0 g (94% of theory) of (5RS,6SR)-8-methoxycarbonyl-8-azabicyclo[4.3.0]non-1-ene-5-carboxylic acid, Melting point: 93°–95° C., ¹H-NMR (CDCl3): δ 10.5–9.50 (m, 1H), 5.65 (m, 1H), 4.08–3.90 (m, 2H), 3.85–3.70 (m, 1H), 3.72 (s, 3H), 3.39 (t, 1H), 3.07–3.00 (m, 1H), 2.95–2.83 (m, 1H), 2.35–2.24 (m, 1H), 2.13–2.01 (m, 2H), 1.88–1.79 ppm (m, 1H).

Example Z 17

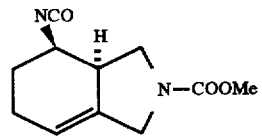

3.0 g (0.01 mol) of (5RS,6SR)-8-methoxycarbonyl-8-azabicyclo[4.3.0]non-1-ene-5-carboxylic acid are initially introduced into 50 ml of toluene, and the mixture is mixed with 1.4 g of triethylamine and 3.8 g of diphenylphosphoryl azide. It is heated at 60° C. for 8 hours, the cooled solution is poured onto ice-water and the organic phase is separated off and extracted several more times with toluene. The combined extracts are dried and concentrated and the residue is used for the following reaction without further purification.

Crude yield: 5.2 g of a brown oil which comprises, as the main constituent, a mixture of (5RS,6SR)- and (5RS,6RS) -8-methoxycarbonyl-8-azabicyclo[4.3.0]non-1-en-5-yl isocyanate, IR: 2150 and 2250 cm⁻¹

Example Z 18

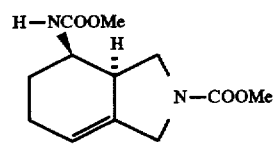

5.2 g of crude (5RS,6SR)-8-methoxycarbonyl-8-azabicyclo[4.3.0]non-1-ene-5-isocyanate are dissolved in 70 ml of methanol and the solution is heated under reflux for 15 hours. The cooled mixture is concentrated and the residue is chromatographed over silica gel with a mixture of cyclohexane and acetone (2:1).

Yield: 1.6 g (45% of theory, based on the acid) of methyl (5RS,6SR)-5-methoxycarbonylamino-8-azabicyclo[4.3.0] non-1-ene-8-carboxylate, Melting point: 113°–117° C., ¹H-NMR (CDCl₃): δ 5,65 (m, 1H), 4.71 (m, 1H), 4.25 (m, 1H), 4.07–3.70 (m, 3H), 3.69 (s, 3H), 3.65 (s, 3H), 3.50 (m, 1H), 3.08 (dt, 1H), 2.88 (m, 1H), 2.22–2.05 (m, 2H), 2.00–1.87 (m, 1H), 1.75–1.64 ppm (m, 1H).

Example Z 19

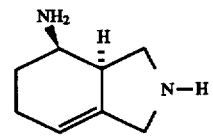

1.20 g (0.005 mol) of methyl (5RS,6SR)-5-methoxycarbonylamino-8-azabicyclo[4.3.0]non-1-ene-8-carboxylate are dissolved in 5 ml of ethanol, and 100 g of a saturated barium hydroxide solution are added. The mixture is heated under reflux for two days and cooled, the barium carbonate which has precipitated out is filtered off and the filtrate is extracted several times with chloroform. The combined organic phases are dried and concentrated.

Yield: 0.60 g (crude yield 92% of theory) of a brown oil: (5RS,6SR)-5-amino-8-azabicyclo[4.3.0]non-1-ene [(3aSR, 4RS)-2,3,3a,4,5,6-hexahydro-1H-isoindol- 4-ylamine], ¹H-NMR (CDCl₃): δ 5.55 (m, 1H), 3.49 (dd, 2H), 3.32 (m, 1H), 3.13 (m, 1H), 2.75 (t, 1H), 2.47–2.59 (m, 1H), 2.10–1.88 (m, 2H), 1.92 (m, 3H), 1.73–1.53 ppm (m, 2H).

PREPARATION OF THE ACTIVE COMPOUNDS

Example 1

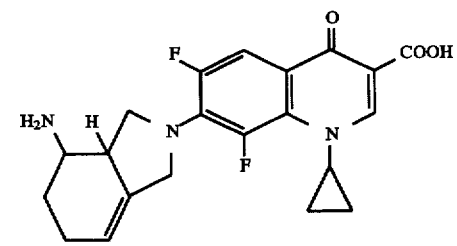

224 mg (2 mmol) of 1,4-diazabicyclo[2.2.2]octane and 152 mg (1:1 mmol) of (3aRS,4RS)-2,3,3a,4,5,6-hexahydro-1H-isoindol-4-ylamine are added to 283 mg (1 mmol) of 1-cyclopropyl-6,7,8-trifluoro-1,4-dihydro24-oxo-3- quinolinecarboxylic acid in a mixture of 2 ml of acetonitrile and 1 ml of dimethylformamide and the mixture is heated under reflux for 1 hour. It is concentrated in vacuo, the residue is stirred with about 40 ml of water and, after drying at 70° C. under a high vacuum, the residue which has precipitated out is purified by chromatography: silica gel, methylene chloride/methanol/17% strength aqueous ammonia (30:8:1).

Yield: 197 mg (49% of theory) of 7-[(3aRS,4RS)-4-amino-2,3,3a,4,5,6-hexahydro-1H-isoindol-2-yl]-1-cyclopropyl-6,8-difluoro-1,4-dihydro-4-oxo-3-quinolinecarboxylic acid, Melting point: 205°–207° C. (with decomposition).

Example 2

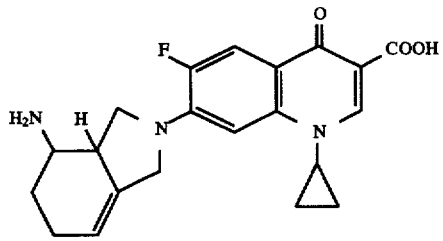

Under conditions corresponding to those in Example 1, 1-cyclopropyl-6,7-difluoro-1,4-dihydro-4-oxo-3-quinolinecarboxylic acid gives 7-[(3aRS,4RS)-4-amino-2,3,3a,4,5,6-hexahydro-1H-isoindol-2-yl]-1-cyclopropyl-6-fluoro-1,4-dihydro-4-oxo-3-quinolinecarboxylic acid of melting point 210°–213° C. (with decomposition) in a yield of 29%.

Example 3

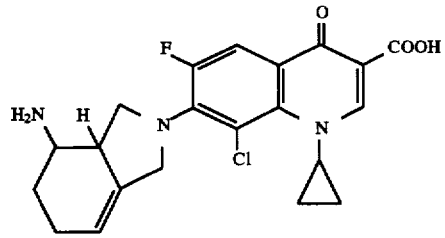

Under conditions corresponding to those in Example 1, 8-chloro-1-cyclopropyl-6,7-difluoro-1,4-dihydro-4oxo-3-quinolinecarboxylic acid gives 7-[(3aRS,4RS)-4-amino-2,3,3a,4,5,6-hexahydro-1H-isoindol-2-yl]-8-chloro-1-cyclopropyl-6-fluoro-1,4-dihydro-4-oxo-3-quinolinecarboxylic acid of melting point 181°–184° C. (with decomposition) in a yield of 85%.

Example 4

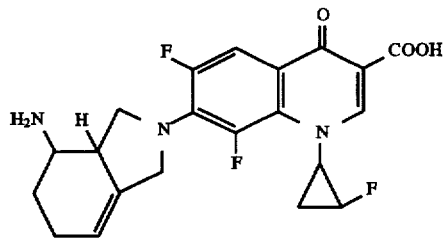

Under conditions corresponding to those in Example 1, 6,7,8-trifluoro-1-(cis-2-fluorocyclopropyl)-1,4-dihydro-4-oxo-3-quinolinecarboxylic acid gives 7-[(3aRS,4RS)-4-amino-2,3,3a,4,5,6-hexahydro-1H-isoindol-2-yl]-6,8-difluoro-1-(cis-2-fluorocyclopropyl)-1,4-dihydro-4-oxo-3-quinolinecarboxylic acid of melting point 210°–205° C. (with decomposition) in a yield of 68%.

Example 5

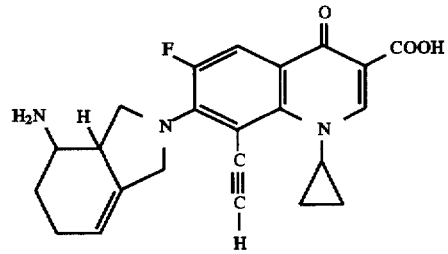

Under conditions corresponding to those in Example 1, 1-cyclopropyl-8-ethinyl-6,7-difluoro-1,4-dihydro-4oxo-3-quinolinecarboxylic acid gives 7-[(3aRS,4RS)-4-amino-2,3,3a,4,5,6-hexahydro-1H-isoindol-2-yl]-1-cyclopropyl-8-ethinyl-6-fluoro-1,4-dihydro-4-oxo-3-quinolinecarboxylic acid of melting point 270°–274° C. (with decomposition) in a yield of 77%.

Example 6

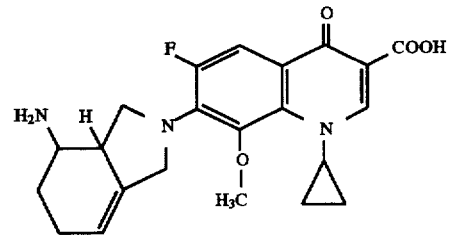

Under conditions corresponding to those in Example 1, 1-cyclopropyl-6,7-difluoro-1,4-dihydro-8-methoxy-4-oxo-3-quinolinecarboxylic acid gives 7-[(3aRS,4RS)-4-amino-2,3,3a,4,5,6-hexahydro-1H-isoindol-2-yl]-1-cyclopropyl-6-fluoro-1,4-dihydro-8-methoxy-4-oxo-3-quinolinecarboxylic acid of melting point 236°–238° C. (with decomposition) in a yield of 67%.

Example 7

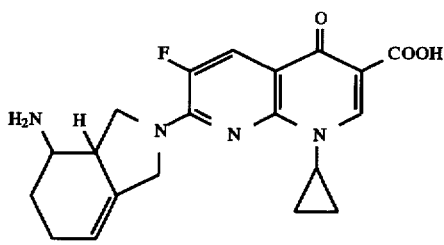

332 mg (2.4 mmol) of (3aRS,4RS)-2,3,3a,4,5,6-hexahydro-1H-isoindol-4-ylamine are added to 283 mg (1 mmol) of 7-chloro-1-cyclopropyl-6-fluoro-1,4-dihydro-4-oxo-1,8-naphthyridine-3-carboxylic acid in 6 ml of acetonitrile and the mixture is healed at 50° C. for 1 hour. The precipitate which has separated out is filtered off with suction, washed with acetonitrile and purified by chromatography: silica gel, methylene chloride/methanol/17% strength aqueous ammonia (30:8:1).

Yield: 76 mg (20% of theory) of 7-[(3aRS,4RS)-4-amino-2,3,3a,4,5,6-hexahydro-1H-isoindol-2-yl]-1-cyclopropyl-6-fluoro-1,4-dihydro-4-oxo-1,8-naphthyridine-3-carboxylic acid, Melting point: 263°–265° C. (with decomposition).

Example 8

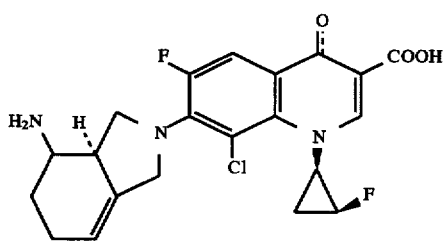

Under conditions corresponding to those in Example 1, 8-chloro-6,7-difluoro-1-[(1R,2S)-2-fluoro-cyclopropyl]-1,4-dihydro-4-oxo-3-quinolinecarboxylic acid and (3aSR,4RS)-2,3,3a,4,5,6-hexahydro-1H-isoindol-4-ylamine give 7-[(3aSR,4RS)-4-amino-2,3,3a,4,5,6-hexahydro-1H-isoindol-2-yl]-8-chloro-6-fluoro-1-[(1R,2S)-2-fluorocyclopropyl]-1,4-dihydro-4-oxo-3-quinolinecarboxylic acid as a crude product, in a yield of 84%, which is purified by chromatography over silica gel (mobile phase: methylene chloride/methanol/17% strength aqueous ammonia 30:8:1);

Melting point: from 192° C. (with decomposition).

Example 9

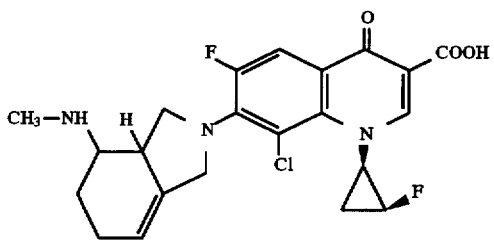

Under conditions corresponding to those in Example 1, 8-chloro-6,7-difluoro-1-[(1R,2S)-2-fluoro-cyclopropyl]-1, 4-dihydro-4-oxo-3-quinolinecarboxylic acid and (3aRS, 4RS)-2,3,3a,4,5,6-hexahydro-1H-isoindol-4-yl-methylamine give a diastereomer mixture of 8-chloro-6-fluoro-1-[(1R,2S)-2-fluorocyclopropyl]-1,4-dihydro-7-[(3aRS,4RS)-4-methylamino-2,3,3a,4,5,6-hexahydro-1H-isoindol-2-yl]-4-oxo-3-quinolinecarboxylic acid, in a yield of 75%, which can be separated by chromatography over silica gel, elution first being carried out with the mobile phase system methylene chloride/methanol (95:5), and the system then being changed to the system methylene chloride/methanol/17% strength ammonia (30:8:1). After concentration of the corresponding fractions, the two diastereomers are obtained in yields of 22% and, respectively, 25% of theory:

A. R$_f$ value: 0.28; silica gel, methylene chloride/methanol/17% strength ammonia (30:8:1); FAB mass spectrum: m/e: 450 [(M+H)$^+$].

B. R$_f$ value: 0.19; silica gel, methylene chloride/methanol/17% strength ammonia (30:8:1); FAB mass spectrum: m/e: 450 [(M+H)$^+$].

Example 10

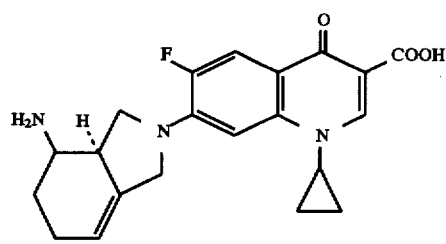

85 mg (0.76 mmol) of 1,4-diazabicyclo[2.2.2]octane and 90 mg (0.65 mmol) of (3aSR,4RS)-2,3,3a,4,5,6-hexahydro-1H-isoindol-4-ylamine are added to 133 mg (0.5 mmol) of 1-cyclopropyl-6,7-difluoro-1,4-dihydro-4-oxo-3-quinolinecarboxylic acid in a mixture of 2 ml of acetonitrile and 1 ml of dimethylformamide, and the mixture is heated under reflux for 1 hour. It is concentrated at 60° C./15 mbar, the residue is treated with about 20 ml of water in an ultrasonic bath and the precipitate which has separated out is filtered off with suction, washed with water and dried at 100° C. in vacuo.

Yield: 108 mg (56% of theory) of 7-[(3aSR,4RS) 4 amino-2,3,3a,4,5,6-hexahydro-1H-isoindol-2-yl]-1-cyclopropyl-6-fluoro-1,4-dihydro-4-oxo-3-quinolinecarboxyic acid, Melting point: 262°–264° C. (with decomposition).

We claim:

1. Compounds of the formula (I)

T—Q  (I)

in which

Q denotes a radical of the formula

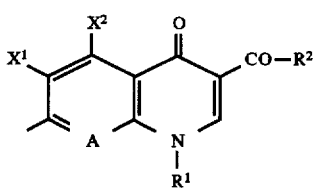

wherein

R¹ represents alkyl which has 1 to 4 carbon atoms and is optionally mono- or disubstituted by halogen or hydroxyl, alkenyl having 2 to 4 carbon atoms, cycloalkyl which has 3 to 6 carbon atoms and is optionally substituted by 1 or 2 fluorine atoms, bicyclo[1.1.1]-pent-1-yl, 1,1-dimethylpropargyl, 3-oxetanyl, methoxy, amino, methylamino, dimethylamino or phenyl which is optionally mono- or disubstituted by halogen, amino or hydroxyl, R² represents hydroxyl, alkoxy which has 1 to 3 carbon atoms and is optionally substituted by hydroxyl, methoxy, amino or dimethylamino, benzyloxy or (5-methyl-2-oxo-1,3-dioxo-4-yl)methyloxy, acetoxymethyloxy, pivaloyloxymethyloxy, 5-indanyloxy), phthalidinyloxy, 3-acetoxy-2-oxo-butyloxy, nitromethyl or dialkoxycarbonylmethyl having 1 to 2 carbon atoms in each alkyl part, X¹ represents hydrogen, halogen or nitro, X² represents hydrogen, halogen, amino, hydroxyl, methoxy, mercapto, methyl, halogenomethyl or vinyl, A represents N or C—R⁷, wherein R⁷ represents hydrogen, halogen, CF₃, OCH₃, OCHF₂, CH₃, CN, CH═CH₂ or C≡CH, or together with R¹ can also form a bridge having the structure —*O—CH₂—CH—CH₃, —*S—CH₂—CH₂—, —*S—CH₂—CH—CH₃, —*CH₂—CH₂—CH—CH₃ or —*O—CH₂—N—R⁸, wherein the atom labelled with * is linked to the carbon atom of A and wherein R⁸ denotes hydrogen, methyl or formyl, and T denotes a radical of the formula

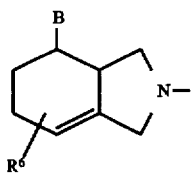

wherein

B represents (CH₂)ₘ—NR³R⁴ or (CH₂)ₘ—OR⁵, wherein m represents 0 or 1,

R³ represents hydrogen, alkyl which has 1 to 3 carbon atoms and is optionally substituted by hydroxyl, acyl having 1 to 3 carbon atoms or alkoxycarbonyl having 1 to 4 carbon atoms in the alkyl part, R⁴ represents hydrogen or methyl and R⁵ represents hydrogen or methyl and R⁶ represents hydrogen or methyl, and pharmaceutically usable hydrates and acid addition salts thereof, as well as the alkali metal, alkaline earth metal, silver and guanidinium salts of the underlying carboxylic acids.

2. Compounds of the formula (I) according to claim 1, in which

Q denotes a radical of the formula

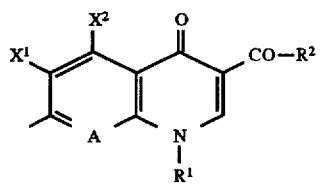

wherein

R¹ represents alkyl which has 1 to 4 carbon atoms and is optionally mono- or disubstituted by halogen, alkenyl having 2 to 3 carbon atoms, cycloalkyl which has 3 or 4 carbon atoms and is optionally substituted by 1 fluorine atom, bicyclo[1.1.1]pent-1-yl, 1,1-dimethylpropargyl, 3-oxetanyl, methylamino or phenyl which is optionally mono- or disubstituted by fluorine, amino or hydroxyl, R² represents hydroxy, alkoxy, having 1 to 2 carbon atoms, benzyloxy or (5-methyl-2-oxo-1,3-dioxol-4yl)-methyloxy, X¹ represents fluorine or chlorine, X² represents hydrogen, halogen, amino, methyl, trifluoromethyl or vinyl, A represents N or C—R⁷, wherein R⁷ represents hydrogen, halogen, CF₃, OCH₃, OCHF₂, CH₃, CN, CH═CH₂ or C≡CH, or together with R¹ can also form a bridge having the structure —*O—CH₂—CH—CH₃, —*S—CH₂—CH₂—, —*CH₂—CH₂—CH—CH₃ or —*O—CH₂N—R⁸, wherein the atom labelled with * is linked to the carbon atom of A, and wherein R⁸ denotes hydrogen or methyl, and T denotes a radical of the formula

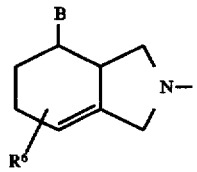

wherein

B represents —NR³R⁴ or —OH, wherein

R³ represents hydrogen or methyl,

R⁴ represents hydrogen or methyl and and pharmaceutically usable hydrates and acid addition salts thereof and the alkali metal, alkaline earth metal, silver and guanidinium salts of the underlying carboxylic acids.

3. Compounds of the formula (I) according to claim 1, in which

T denotes a radical of the formula

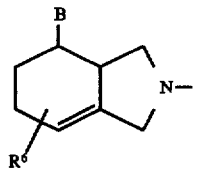

wherein

B represents NH₂ and

R⁶ represents hydrogen, and pharmaceutically usable hydrates and acid addition salts thereof and the alkali metal, alkaline earth metal, silver and guanidinium salts of the underlying carboxylic acids.

4. Diastereomerically pure and enantiomerically pure compounds according to claim 1.

5. An antibacterial composition comprising an antibacterially effective amount of a compound or addition product thereof according to claim 1 and a diluent.

6. A composition according to claim 5 in the form of a tablet, capsule or ampule.

7. A composition according to claim 5 wherein the diluent comprises an animal feed stock.

8. A method of combating bacteria in a patient in need thereof which comprises administering to such patient an antibacterially effective amount of a compound or addition product thereof according to claim 1.

9. The method according to claim 8 wherein such compound is

7-[(3aRS,4RS)-4-amino-2,3,3a,4,5,6-hexahydro-1H-isoindol-2-yl]-1-cyclopropyl-6,8-difluoro-1,4-dihydro-4-oxo-3-quinolinecarboxylic acid 7-[(3aRS,4RS)-4-amino-2,3,3a,4,5,6-hexahydro-1H-isoindol-2-yl]-1-cyclopropyl-6-fluoro-1,4-dihydro-4-oxo-3-quinolinecarboxylic acid 7-[(3aRS,4RS)-4-amino-2,3,3a,4,5,6-hexahydro-1H-isoindol-2-yl]-8-chloro-1-cyclopropyl-6-fluoro-1,4-dihydro-4-oxo-3-quinolinecarboxylic acid or 7-[(3aRS,4RS)-4-amino-2,3,3a,4,5,6-hexahydro-1H-isoindol-2-yl]-6,8-difluoro-1-(cis-2-fluorocyclopropyl)-1,4-dihydro-4-oxo-3-quinolinecarboxylic acid.

* * * * *